US008445251B2

(12) United States Patent
Smith et al.

(10) Patent No.: US 8,445,251 B2
(45) Date of Patent: May 21, 2013

(54) RATIONALLY-DESIGNED SINGLE-CHAIN MEGANUCLEASES WITH NON-PALINDROMIC RECOGNITION SEQUENCES

(75) Inventors: James J. Smith, Durham, NC (US); Derek Jantz, Durham, NC (US)

(73) Assignee: Precision BioSciences, Inc., Durham, NC (US)

(*) Notice: Subject to any disclaimer, the term of this patent is extended or adjusted under 35 U.S.C. 154(b) by 54 days.

(21) Appl. No.: 12/771,163

(22) Filed: Apr. 30, 2010

(65) Prior Publication Data

US 2010/0311817 A1 Dec. 9, 2010

Related U.S. Application Data

(63) Continuation of application No. PCT/US2008/082072, filed on Oct. 31, 2008.

(60) Provisional application No. 61/001,247, filed on Oct. 31, 2007.

(51) Int. Cl.
C12N 9/16 (2006.01)
C07K 14/00 (2006.01)

(52) U.S. Cl.
USPC ........................ 435/196; 435/195; 530/350

(58) Field of Classification Search
None
See application file for complete search history.

(56) References Cited

U.S. PATENT DOCUMENTS

| | | | |
|---|---|---|---|
| 4,873,316 A | 10/1989 | Meade et al. | |
| 5,384,253 A | 1/1995 | Krzyzek et al. | |
| 6,316,024 B1 | 11/2001 | Allen et al. | |
| 6,379,699 B1 | 4/2002 | Virtanen et al. | |
| 6,387,397 B1 | 5/2002 | Chen et al. | |
| 6,511,676 B1 | 1/2003 | Boulikas | |
| 6,593,308 B2 | 7/2003 | Szoka, Jr. | |
| 7,037,492 B2 | 5/2006 | Glorioso et al. | |
| 7,897,372 B2 | 3/2011 | Duchateau et al. | |
| 8,119,361 B2 | 2/2012 | Smith et al. | |
| 8,124,369 B2 | 2/2012 | Smith et al. | |
| 8,129,134 B2 | 3/2012 | Smith et al. | |
| 8,133,697 B2 | 3/2012 | Smith et al. | |
| 8,143,015 B2 | 3/2012 | Smith et al. | |
| 8,143,016 B2 | 3/2012 | Smith et al. | |
| 8,148,098 B2 | 4/2012 | Smith et al. | |
| 8,163,514 B2 | 4/2012 | Smith et al. | |
| 2004/0002092 A1 | 1/2004 | Arnould et al. | |
| 2006/0078552 A1 | 4/2006 | Arnould et al. | |

FOREIGN PATENT DOCUMENTS

| | | |
|---|---|---|
| EP | 0264166 A1 | 4/1988 |
| WO | WO-03078619 A1 | 9/2003 |
| WO | WO-2004067736 A2 | 8/2004 |
| WO | WO-2004067753 A2 | 8/2004 |
| WO | WO-2005105989 A1 | 11/2005 |
| WO | WO-2006097784 A1 | 9/2006 |
| WO | WO-2006097853 A1 | 9/2006 |
| WO | WO-2006097854 A1 | 9/2006 |
| WO | WO-2007034262 A1 | 3/2007 |
| WO | WO-2007047859 A2 | 4/2007 |
| WO | WO-2007049095 A1 | 5/2007 |
| WO | WO-2007049156 A2 | 5/2007 |
| WO | WO-2007057781 A2 | 5/2007 |
| WO | WO-2007060495 A1 | 5/2007 |
| WO | WO-2007093836 A1 | 8/2007 |
| WO | WO-2007093918 A2 | 8/2007 |
| WO | WO-2008010009 A1 | 1/2008 |
| WO | WO-2008059317 A1 | 5/2008 |
| WO | WO-2008059382 A2 | 5/2008 |
| WO | WO-2008093152 A1 | 8/2008 |
| WO | WO-2008093249 A2 | 8/2008 |
| WO | WO-2008102198 A1 | 8/2008 |
| WO | WO-2008102274 A2 | 8/2008 |
| WO | WO-2008152523 A1 | 12/2008 |
| WO | WO-2009006297 A2 | 1/2009 |
| WO | WO-2009059195 A2 | 5/2009 |
| WO | WO-2009074873 A1 | 6/2009 |
| WO | WO-2009095793 A1 | 8/2009 |

OTHER PUBLICATIONS

Adler, David A. et al. "Bioinformatics." Encyclopedia of Life Sciences. John Wiley & Sons Ltd. No month listed—2001, pp. 1-8.

Argast et al., I-Ppol and I-Crel homing site sequence degeneracy determined by random mutagenesis and sequential in vitro enrichment, J. Mol. Biol., 1998, pp. 345-353, vol. 280.

Bibikova et al., Stimulation of homologous recombination through targeted cleavage by chimeric nucleases, Molecular and Cellular Biology, Jan. 2001, pp. 289-297, vol. 21 No. 1.

Cellectis Press Communication of Genome Modification Technology. Sep. 1, 2009. 2 pages.

Chevalier et al., The homing endonuclease I-Crel uses three metals, one of which is shared between the two active sites, Nature Structural Biology, Apr. 2001, pp. 312-316, vol. 8 No. 4.

Communication from the European Patent Office for Opposition to European Pat. No. 1 485 475 on Apr. 14, 2010. 4 pages.

Communication from the European Patent Office for Opposition to European Pat. No. 1 485 475 regarding Decision of the Opposition Division on Jan. 26, 2010. 2 pages.

Communication from the European Patent Office for Opposition to European Pat. No. 1 485 475 regarding Interlocutory Decision in Opposition on Feb. 8, 2010. 114 pages.

Communication from the European Patent Office for Opposition to European Pat. No. 1 485 475 regarding Minutes of the Oral Proceedings on Nov. 18, 2009. 81 pages.

Communication from the European Patent Office for Opposition to European Pat. No. 1 485 475 regarding Brief Communication dated Oct. 1, 2009. 1 page.

(Continued)

*Primary Examiner* — Richard Hutson

(74) *Attorney, Agent, or Firm* — Wilmer Cutler Pickering Hale and Dorr LLP

(57) ABSTRACT

Disclosed are rationally-designed, non-naturally-occurring meganucleases in which a pair of enzyme subunits having specificity for different recognition sequence half-sites are joined into a single polypeptide to form a functional heterodimer with a non-palindromic recognition sequence. The invention also relates to methods of producing such meganucleases, and methods of producing recombinant nucleic acids and organisms using such meganucleases.

1 Claim, 1 Drawing Sheet

OTHER PUBLICATIONS

Communication from the European Patent Office for Opposition to European Pat. No. 1 485 475 regarding Brief Communication dated Oct. 7, 2009. 1 page.

Communication from the European Patent Office in Opposition to European Pat. No. 1 485 475 regarding Summons to Oral Proceedings dated Jun. 30, 2009. 9 pages.

Communication from the European Patent Office transmitting Third Party Observations for European Pat. No. 1 485 475 dated Nov. 5, 2009. 8 pages.

Communication of Notices of Opposition from the European Patent Office in Opposition to European Pat. No. 1 485 475 dated Jul. 10, 2008. 1 page.

Cozzone, Alain J. "Proteins: Fundamental Chemical Properties." Encyclopedia of Life Sciences. No month listed—2002. John Wiley & Sons Ltd. pp. 1-10.

Dalgaard, Jacob Z. et al. "A Site-Specific Endonuclease Encoded by a Typical Archaeal Intron." Proc. Natl. Acad. Sci. Jun. 1993. vol. 90. pp. 5414-5417.

Duan et al., Crystal structure of PI-SceI, a homing endonuclease with protein splicing activity. Cell, May 16, 1997, vol. 89, pp. 555-564.

Example: Generation of I-CreI Single Chain Molecules Based on Engineered Meganucleases. Cited in Opposition to European Pat. No. 1 485 475 on Sep. 22, 2009. 4 pages.

Filing by Opponent in Opposition to European Pat. No. 1 485 475 dated Jan. 3, 2011. 27 pages.

Filing by Opponent in Opposition to European Pat. No. 1 485 475 dated Jun. 17, 2010. 10 pages.

Filing by Proprietor in Opposition to European Pat. No. 1 485 475 dated Dec. 30, 2010. 22 pages.

Filing by Proprietor in Opposition to European Pat. No. 1 485 475 dated Jan. 16, 2009. 35 pages.

Filing by Proprietor in Opposition to European Pat. No. 1 485 475 dated Sep. 22, 2009. 34 pages.

First Declaration of Derek Jantz cited in Opposition to European Pat. No. 1 485 475. Jun. 4, 2008. 10 pages.

Generation of DmoCre Proteins with Flexible Linkers. Cited in Opposition to European Pat. No. 1 485 475 on Dec. 30, 2010. 2 pages.

Grizot et al., "Efficient targeting of a SCID gene by an engineered single-chain homing endonuclease," NAR, 2009, 1-15.

Heath, Patrick J. et al. "The Structure of I-CreI, A Group I Intron-encoded Homing Endonuclease." Nature Structural Biology. vol. 4, No. 6. Jun. 1997. pp. 468-476.

Hu et al. "Probing the Structure of the PI-SceI-DNA Complex by Affinity Cleavage and Affinity Photcross-linking." The Journal of Biological Chemistry. Jan. 28, 2000. vol. 275, No. 4. pp. 2705-2712.

Ichiyanagi et al., Crystal structure of an archaeal intein-encoded homing endonuclease PI-Pful, J. Mol. Biol., 2000, pp. 889-901, vol. 300.

Jacquier et al., "An Intron-Encoded Protein Is Active in a Gene Conversion Process That Spreads an Intron into a Mitochondrial Gene," Cell, 1985, 41, 383-394.

Jurica, M.S. et al. "Homing Endonucleases: Structure, Function and Evolution." CMLS: Cellular and Molecular Life Sciences. Feb. 1999. vol. 55. pp. 1304-1326.

Li et al., "Generation of single-chain LAGLIDADG homing endonucleases from native homodimeric precursor proteins," NAR, 2009, 37, 5, 1650-1662.

Liang et al. "Genetic Fusion of Subunits of a Dimeric Protein Substantially Enhances its Stability and Rate of Folding." Proc. Natl. Acad. Sci. vol. 90. Aug. 1993. pp. 7010-7014.

Lucas et al., Rapid evolution of the DNA-binding site in LAGLIDADG homing endonucleases, Nucleic Acids Research, 2001, pp. 960-969, vol. 29 No. 4.

Moure et al., Crystal structure of the intein homing endonuclease PI-SceI bound to its recognition sequence, Nature Structural Biology, Oct. 2002, pp. 764-770, vol. 9 No. 10.

New Example of DmoCre Meganuclease Cleaving RGI.10.2D34 DNA Target. Cited in Opposition to European Pat. No. 1 485 475 on Jan. 16, 2009. 6 pages.

New Example of Single Chain Meganuclease Cleaving the RAG1 Gene. Cited in Opposition to European Pat. No. 1 485 475 on Jan. 16, 2009. 6 pages.

New Example of Single Chain Meganuclease Cleaving XPC Gene. Cited in Opposition to European Pat. No. 1 485 475 on Jan. 16, 2009. 8 pages.

Notice of Appeal filing by Opponent in Opposition to European Pat. No. 1 485 475 dated Apr. 7, 2010. 4 pages.

Notice of Appeal filing by Proprietor in Opposition to European Pat. No. 1 485 475 dated Apr. 9, 2010. 2 pages.

Notice of Opposition filing by Opponent from the European Patent Office in Opposition to European Pat. No. 1 485 475 dated Jun. 5, 2008. 33 pages.

Notice of Opposition filing by Proprietor in Opposition to European Pat. No. 1 485 475 dated Nov. 3, 2008. 2 pages.

Opposition Procedure filing by Proprietor in Opposition to European Pat. No. 1 485 475 dated Nov. 17, 2009. 3 pages.

Pace, C. Nick et al. "Protein Stability." Encyclopedia of Life Sciences. No month listed—2001. John Wiley & Sons Ltd. pp. 1-4.

Perrin, M. Arnaud. Presentation on Jul. 7, 1994. 23 pages.

Poland, Bradley W. et al. "Structural Insights into the Protein Splicing Mechanism of PI-SceI." The Journal of Biological Chemistry. Jun. 2000. vol. 275, No. 22. pp. 16408-16413.

Sali et al. "Comparative Protein Modeling by Satisfaction of Spatial Restraints." J. Mol. Biol. Jul. 1993. pp. 779-815.

Second Declaration of Derek Jantz cited in Opposition to European Pat. No. 1 485 475. Sep. 18, 2009. 51 pages.

Seligman et al., Genetic Analysis of the *Chlamydomonas reinhardtii* I-CreI mobile intron homing system in *Escherichia coli*, Genetics, Dec. 1997, pp. 1653-1664, vol. 147.

Silva et al., Crystal structure of the thermostable archaeal intron-encoded endonuclease I-Dmol, J. Mol. Biol., 1999, pp. 1123-1136, vol. 286.

Silva, George H. et al. "From Monomeric to Homodimeric Endonucleases and Back: Engineering Novel Specificity of LAGLIDADG Enzymes." J. Mol. Biol. Jul. 2006. pp. 744-754.

Sourdive, David J.D. et al. L'association Francaise Contre les Myopathies et Cellectis Lancent un Programme de Chirurgle Genomique Pour Guerir Les Maladies Genetiques. Cited in Opposition to European Pat. No. 1 485 475 on Jan. 16, 2009. 3 pages.

Statement of Grounds of Appeal filing by Proprietor in Opposition to European Pat. No. 1 485 475 dated Jun. 10, 2010. 60 pages.

Submission of Declaration by Derek Jantz by Opponent in Opposition to European Pat. No. 1 485 475 dated Nov. 11, 2009. 10 pages.

Submission of List of References by Opponent in Opposition to European Pat. No. 1 485 475 dated Nov. 16, 2009. 3 pages.

Third Declaration of Derek Jantz cited in Opposition to European Pat. No. 1 485 475. Nov. 11, 2009. 9 pages.

Turmel, Monique et al. "Evolutionary Conserved and Functionally Important Residues in the I-Ceul Homing Endonuclease." Nucleic Acid Research. Apr. 1997. vol. 25, No. 13. pp. 2610-2619. 10 pages.

Werner, Erik et al. "High Resolution Crystal Structure of Domain I of the *Saccharomyces cerevisiae* Homing Endonuclease PI-SceI." Nucleic Acid Research. Jul. 2002. vol. 30, No. 18. pp. 3962-3971. 10 pages.

Wild-type Sequence of I-CreI. Cited in Opposition to European Pat. No. 1 485 475 on Jan. 16, 2009. 1 page.

Yeast Activity Assay of the LAM1/LAM2 Meganuclease. Cited in Opposition to European Pat. No. 1 485 475 on Jan. 16, 2009 and Sep. 22, 2009. 5 pages.

Altschul, et al., "Basic Local Alignment Search Tool", J. Mol. Biol., 215:403-410 (1990).

Altschul, et al., "Gapped BLAST and PSI-BLAST; A New Generation of Protein Database Search Programs", Nucleic Acids Research, 25(17):3389-3402 (1997).

Arnould, "Engineering of Large Numbers Of Highly Specific Homing Endonucleases that Induce Recombination on Novel DNA Targets", J. Mol. Biol., 355:443-458 (2006).

Arnould, et al., "Engineered I-CreI Derivatives Cleaving Sequences from the Human XPC Gene can Induce Highly Efficient Gene Correction in Mammalian Cells", J. Mol. Biol., 371:49-65 (2007).

Aurora, et al., "Helix Capping", Protein Science, 7:21-38 (1998).

Banerji, et al., "A Lymphocyte-Specific Cellular Enhancer is Loacated Downstream of the Joining Region in Immunoglobulin Heavy Chain Genes", Cell, 33:729-740 (1983).

Bmerc, "The PSA Protein Structure Prediction Server", http://bmerc-www/bi/edu/psa/, downloaded Mar. 3, 2011 (3 pages).

Brodelius, et al., "Fusion of Farnesyldiphosphate Synthase and epi-aristolochene Synthase, a Sesquiterpene Cyclase Involved in Capsidiol Biosynthesis in Nicotiana Tabacum", Eur. J. Biochem., 269:3570-3577 (2002).

Byrne, et al., "Multiplex Gene Regulation: A Two-Tiered Approach to Transgene Regulation in Transgenic Mice", Proc. Natl. Acad. Sci. USA, 86:5473-5477 (1989).

Cahill, et al., "Mechanisms of Eukaryotic DNA Double Strand Break Repair", Frontiers in Bioscience, 11:1958-1976 (2006).

Calame, et al., "Transcriptional Controlling Elements in the Immunoglobulin and T Cell Receptor Loci", Advances in Immunology, 43:235-275 (1988).

Camper, et al., "Postnatal Repression of the Alpha-Fetoprotein Gene is Enhancer Independent", Genes & Development, 3:537-546 (1989).

Chames, et al., "In vivo Selection of Engineered Homing Endonucleases using Double-Strand Break Induced Homologous Recombination", Nucleic Acids Research, vol. 33, No. 20 (2005) (10 pages).

Chevalier, et al., "Design, Activity, and Structure of a Highly Specific Artificial Endonuclease", Molecular Cell, 10:895-905 (2002).

Chevalier, et al., "Homing Endonucleases: Structural and Functional Insight into the Catalysts of Intron/Intein Mobility", Nucleic Acids Research, 29(18):3757-3774 (2001).

Chevalier, et al., "Metal-Dependent DNA Cleavage Mechanism of the I-CreI LAGLIDADG Homing Endonuclease", Biochemistry, 43:14015-14026 (2004).

Chilton, et al., "Targeted Integration of T-DNA into the Tobacco Genome at Double-Stranded Breaks: New Insignts on the Mechanism of T-DNA Integration", Plant Pyhsiology, 133:956-965 (2003).

Clapp, "Somatic Gene Therapy into Hematopoietic Cells: Curent Status and Future Implications", Current Controversies in Perinatal Care II, 20(1):155-168 (1993) (16 pages).

Curiel, et al., "Adenovirus Enhancement of Transferrin-Polylysine-Mediated Gene Delivery", Proc. Natl. Acad. Sci. USA, 88:8850-8854 (1991).

Curiel, et al., "High-Efficiency Gene Transfer Mediated by Adenovirus Coupled to DNA-Polylysine Complexes", Human Gene Therapy, 3:147-154 (1992).

Edlund, et al., "Cell-Specific Expression of the Rat Insulin Gene: Evidence for Role of Two Distinct 5' Flanking Elements", Science, 230:912-916 (1985).

Eglitis, et al., "Retroviral Vectors for Introduction of Genes into Mammalian Cells", Biotechniques, 6(7):608-614 (1988) (8 pages).

Eglitis, et al., "Retroviral-Mediated Gene Transfer Into Hemopoietic Cells", *Molecular Biology of Hemopoiesis*, Plenum Press, New York, pp. 19-27 (1987) (11 pages).

Epinat, et al., "A Novel Engineered Meganuclease Induces Homologous Recombination in Yeast and Mammalian Cells", Nucleic Acids Research, 31(11):2952-2962 (2003).

Fajardo-Sanchez, et al., "Computer Design of Obligate Heterodimer Meganucleases Allows Efficient Cutting of Custom DNA Sequences", Nucleic Acids Research, 36(7):2163-2173 (2008).

Fersht, *Structure and Mechanism in Protein Science: A Guide to Enzyme Catalysis and Protein Folding*, WH Freeman and Company, New York, (1999) (17 pages).

Fromm, et al., "Expression of Genes Transferred into Monocot and Dicot Plant Cells by Electroporation", Proc. Natl. Acad. Sci. USA, 82:5824-5828 (1985).

Fynan, et al., "DNA Vaccines: Protective Immunizations by Parenteral, Mucosal, and Gene-Gun Inoculations", Proc. Natl. Acad. Sci. USA, 90:11478-11482 (1993).

Gish, et al., "Identification of Protein Coding Regions by Database Similarity Search", Nature Genetics, 3:266-272 (1993).

Gossler, et al., "Transgenesis by Means of Blastocyst-Derived Embryonic Stem Cell Lines", Proc. Natl. Acad. Sci. USA, Developmental Biology, 83:9065-9069 (1986).

Gouble, et al., "Efficient in toto Targeted Recombination in Mouse Liver by Meganuclease-Induced Double-Strand Break", The Journal of Gene Medicine, 8:616-622 (2006).

Graham, et al., "Transformation of Rat Cells by DNA of Human Adenovirus 5", Virology, 54:536-539 (1973).

Gremillon, et al., "New Plant Growth-Modifying Properties of the Agrobacterium T-6b Oncogene Revealed by the use of a Dexamethasone-inducible Promoter", The Plant Journal, 37:218-228 (2004).

Hudecz, et al., "Medium-Sized Peptides as Built in Carriers for Biologically Active Compounds", Medicinal Research Reviews, 25(6):679-736 (2005).

Johnston, et al., "Chapter 17: Gene Gun Transfection of Animal Cells and Genetic Immunization", *Methods in Cell Biology*, vol. 43, Academic Press, Inc., pp. 353-365 (1994).

Jurica, et al., "DNA Recognition and Cleavage by the LAGLIDADG Homing Endonuclease I-CreI", Molecular Cell, 2:469-476 (1998).

Kessel, et al., "Murine Developmental Control Genes", Science, 249:374-379 (1990).

Kim, et al., "Hybrid Restriction Enzymes: Zinc Finger Fusions to Fok I Cleavage Domain", Proc. Natl. Acad. Sci. USA, 93:1156-1160 (1996).

Korman, et al., "Expression of Human Class II Major Histocompatibility Complex Antigens using Retrovirus Vectors", Proc. Natl. Acad. Sci. USA, 84:2150-2154 (1987).

Lasic, et al., "Liposomes Revisited", Science, 267:1276-1276 (1995).

Lu, et al., "High Efficiency Retroviral Mediated Gene Transduction into Single Isolated Immature and Replatable DC34$^{3+}$ Hematopoietic Stem/Progenitor Cells from Human Umbilical Cord Blood", J. Exp. Med, 178:2089-2096 (1993).

Mack, et al., "A Small Bispecific Antibody Construct Expressed as a Functional Single-Chain Molecule with High Tumor Cell Cytotoxicity", Proc. Natl. Acad. Sci. USA, 92:7021-7025 (1995).

Madden, et al., "Applications of Network BLAST Server", Methods in Enzymology, 266:131-141 (1996).

McDaniel, et al., "Advances in Synthetic Biology: On the Path from Prototypes to Applications", Current Opinions in Biotechnology, 16:476-483 (2005).

Monnat, et al., "Generation of Highly Site-Specific DNA Double-Strand Breaks in Human Cells by the Homing Endonucleases I-PpoI and I-CreI", Biochemical and Biophysical Research Communications, 255:88-93 (1999).

Omirulleh, et al., "Activity of a Chimeric Promoter with the Double CaMV 35S Enhancer Element in Protoplast-Derived Cells and Transgenic Plants in Maize", Plant Molecular Biology, 21:415-428 (1993).

Papworth, et al, "Designer Zind-Finger Proteins and their Applications", Gene 366:27-38 (2006).

Pfeiffer, et al., "Lipoplex Gene Transfer of Inducible Nitric Oxide Synthases Inhibits the Reactive Intimal Hyperplasia After Expanded Polytetrafluoroethylene Bypass Grafting", Journal of Vascular Surgery, 43(5):1021-1027 (2006).

Pinkert, et al., "An Albumin Enhancer Located 10 kb Upstream Functions along with its Promoter to Direct Efficieint, Liver-Specific Expression in Transgenic Mice", Genes & Development, 1:268-276 (1987).

Porteus, "Mammalian Gene Targeting with Designed Zinc Finger Nucleases", Molecular Therapy, 13(2):438-446 (2006).

Porteus, et al., "Gene Targeting Using Zinc Finger Nucleases", Nature Biotechnology, 23(8):967-973 (2005).

Prieto, et al., "The C-terminal Loop of the Homing Endonuclease I-CreI is Essential for Site Recognition, DNA Binding and Cleavage", Nucleic Acids Research, 35(10):3262-3271 (2007).

Puchta, et al., "Two Different but Related Mechanisms are Used in Plants for the Repair of Genomic Double-Strand Breaks by Homologous Recombination", Proc. Natl. Acad. Sci. USA, 93:5055-5060 (1996).

Queen, et al., "Immunoglobulin Gene Transcription Is Activated by Downstream Sequence Elements", Cell, 33:741-748 (1983).

Rong, et al, "Targeted Mutagenesis by Homologous Recombination of D. Melanogaster", Genes and Development, 16:1568-1581 (2002) (15 pages).

Rosen, et al., "Homing Endonuclease I-CreI Derivatives with Novel DNA Target Specificities", Nucleic Acids Research, 34(17):4791-4800 (2006).

Rouet, et al., "Introduction of Double-Strand Breaks into the Genome of Mouse Cells by Expression of a Rare-Cutting Endonuclease", Molecular and Cellular Biology, 14(12):8096-8106 (1994).

Rui, et al., "Transfer of Anti-TFAR19 Monoclonal Antibody into HeLa Cells by in situ Electroporation Can Inhibit the Apoptosis", Life Sciences, 71:1771-1778 (2002).

Salomon, et al., "Capture of Genomic and T-DNA Sequences During Double-Strand Break Repair in Somatic Plant Cells", EMBO Journal, 17(20):6086-6095 (1998).

Sanger, et al., "DNA Sequencing with Chain-Terminating Inhibitors", Proc. Natl. Acad. Sci. USA, 74(12):5463-5468 (1977).

Seligman, et al., "Mutations Altering the Cleavage Specificity of a Homing Endonuclease", Nucleic Acids Research, 30(17):3870-3879 (2002).

Singh, et al., "Isolation and Characterization of a Flowering Plant Male Gametic Cell-Specific Promoter", FEBS Letters, 542:47-52 (2003).

Smith, et al., "A Combinatorial Approach to Create Artificial Homing Endonucleases Cleaving Chosen Sequences", Nucleic Acids Research, vol. 34, No. 22 (2006) (12 pages).

Smith, et al., "Requirements for Double-Strand Cleavage by Chimeric Restriction Enzymes with Zinc Finger DNA-Recognition Domains", Nucleic Acids Research, 28(17):3361-3369 (2000).

Spiegel, et al., "The Structure of I-Ceul Homing Endonuclease: Evolving Asymmetric DNA Recognition from a Symmetric Protein Scaffold", Structure, 14:869-880 (2006).

Stoddard, "Homing Endonuclease Structure and Function", Quarterly Reviews of Biophysics, 38:49-95 (2006).

Sussman, et al., Isolation and Characterization of New Homing Endonuclease Specificities at Individual Target Site Positions, J. Mol. Biol., 342:31-41 (2004).

Tzfira, et al., "Towards Targeted Mutagenesis and Gene Replacement in Plants", TRENDS in Biotechnologh, 23(12):567-569 (2005).

Ueda, et al., "Cell-Growth Control by Monomeric Antigen: the Cell Surface Expression of Lysozyme-Specific Ig V-domains Fused to Truncated Epo Receptor", Journal of Immunological Methods, 241:159-170 (2000).

Urnov, et al., "Highly Efficient Endogenous Human Gene Correction Using Designed Zinc-Finger Nucleases", Nature, 435:646-651 (2005).

Van Der Giessen, et al., "Comparison of the 23S Ribosomal RNA Genes and the Spacer Region Between the 16S and 23S rRNA Genes of the Closely Related Mycobacterium avium and Mycobacterium paratuberculosis and the Fast-Growing Mycobacterium Pheli", Microbiology, 140:1103-1108 (1994).

Wagner, et al., "Coupling of Adenovirus to Transferrin-Polylysine/DNA Conmplexes Greatly Enhances Receptor-Mediated Gene Delivery and Expression of Transfected Genes", Proc. Natl. Acad. Sci., 89:6099-6103 (1992).

Winoto, et al., "A Novel, Inducible and T Cell-Specific Enhancer Located at the 3' End of the T Cell Receptor α Locus", EMBO Journal, 8(3):729-733 (1989).

Wong, et al., "Electric Field Mediated Gene Transfer", Biochemical and Biophysical Research Communications, 107(2):584-587 (1982).

Wright, et al., "High-Frequency Homologous Recombination in Plants Mediated by Zinc-Finger Nucleases", The Plant Journal, 44:693-705 (2005).

Young, et al., "Gene Therapy for Oral Cancer: Efficient Delivery of a 'Suicide Gene' to Murine Oral Cancer Cells in Physiological Milieu", CDA Journal, 33(12):967-971 (2005).

Zatloukal, et al., "Transferrinfection: A Highly Efficient Way to Express Gene Constructs in Eukaryotic Cells", Annals New York Academy of Sciences, pp. 136-153 (1992).

Zhang, et al., "A Greedy Algorithm for Aligning DNA Sequences", Journal of Computational Biology, 7(1/2):203-214 (2000) (28 pages).

Extended European Search Report for European Patent Application No. 08845549.8 mailed Dec. 6, 2010. 10 pages.

Supplementary Search Report for European Patent Application No. 08845549.8 mailed Dec. 23, 2010. 8 pages.

International Search Report and Written Opinion issued for PCT/US08/82072, mailed Jul. 20, 2009 (12 pages).

Structural Components of Linker 9
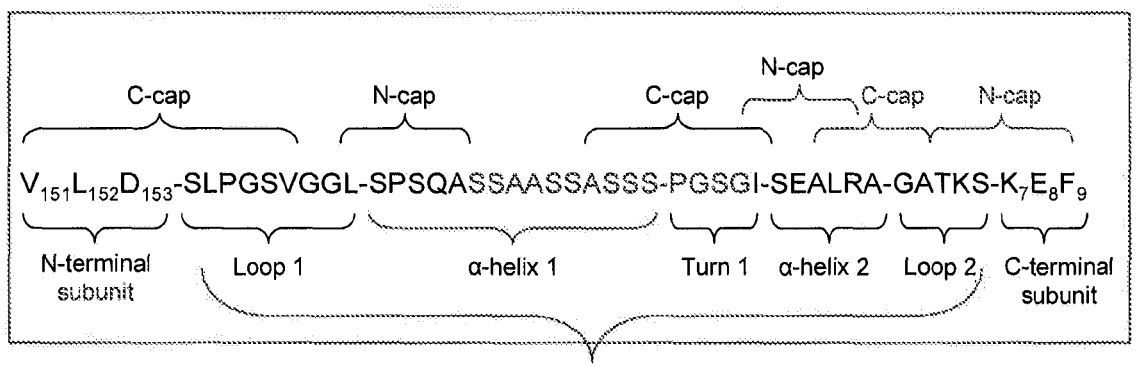
SEQ ID NO: 77

SEQUENCE LISTING

<160> NUMBER OF SEQ ID NOS: 110

<210> SEQ ID NO 1
<211> LENGTH: 163
<212> TYPE: PRT
<213> ORGANISM: Chlamydomonas reinhardtii

<400> SEQUENCE: 1

Met Asn Thr Lys Tyr Asn Lys Glu Phe Leu Leu Tyr Leu Ala Gly Phe

```
                1               5                  10                 15
Val Asp Gly Asp Gly Ser Ile Ile Ala Gln Ile Lys Pro Asn Gln Ser
                        20                 25                 30

Tyr Lys Phe Lys His Gln Leu Ser Leu Thr Phe Gln Val Thr Gln Lys
                35                 40                 45

Thr Gln Arg Arg Trp Phe Leu Asp Lys Leu Val Asp Glu Ile Gly Val
        50                 55                 60

Gly Tyr Val Arg Asp Arg Gly Ser Val Ser Asp Tyr Ile Leu Ser Glu
 65                 70                 75                 80

Ile Lys Pro Leu His Asn Phe Leu Thr Gln Leu Gln Pro Phe Leu Lys
                        85                 90                 95

Leu Lys Gln Lys Gln Ala Asn Leu Val Leu Lys Ile Ile Trp Arg Leu
                100                105                110

Pro Ser Ala Lys Glu Ser Pro Asp Lys Phe Leu Glu Val Cys Thr Trp
            115                120                125

Val Asp Gln Ile Ala Ala Leu Asn Asp Ser Lys Thr Arg Lys Thr Thr
                130                135                140

Ser Glu Thr Val Arg Ala Val Leu Asp Ser Leu Ser Glu Lys Lys Lys
145                150                155                160

Ser Ser Pro
```

<210> SEQ ID NO 2
<211> LENGTH: 170
<212> TYPE: PRT
<213> ORGANISM: Monomastix sp.

<400> SEQUENCE: 2

```
Met Thr Thr Lys Asn Thr Leu Gln Pro Thr Glu Ala Ala Tyr Ile Ala
 1               5                  10                 15

Gly Phe Leu Asp Gly Asp Gly Ser Ile Tyr Ala Lys Leu Ile Pro Arg
                        20                 25                 30

Pro Asp Tyr Lys Asp Ile Lys Tyr Gln Val Ser Leu Ala Ile Ser Phe
                35                 40                 45

Ile Gln Arg Lys Asp Lys Phe Pro Tyr Leu Gln Asp Ile Tyr Asp Gln
        50                 55                 60

Leu Gly Lys Arg Gly Asn Leu Arg Lys Asp Arg Gly Asp Gly Ile Ala
 65                 70                 75                 80

Asp Tyr Thr Ile Ile Gly Ser Thr His Leu Ser Ile Ile Leu Pro Asp
                        85                 90                 95

Leu Val Pro Tyr Leu Arg Ile Lys Lys Gln Ala Asn Arg Ile Leu
                100                105                110

His Ile Ile Asn Leu Tyr Pro Gln Ala Gln Lys Asn Pro Ser Lys Phe
            115                120                125

Leu Asp Leu Val Lys Ile Val Asp Val Gln Asn Leu Asn Lys Arg
                130                135                140

Ala Asp Glu Leu Lys Ser Thr Asn Tyr Asp Arg Leu Leu Glu Glu Phe
145                150                155                160

Leu Lys Ala Gly Lys Ile Glu Ser Ser Pro
                165                170
```

<210> SEQ ID NO 3
<211> LENGTH: 218
<212> TYPE: PRT
<213> ORGANISM: Chlamydomonas moewusii

<400> SEQUENCE: 3

```
Met Ser Asn Phe Ile Leu Lys Pro Gly Glu Lys Leu Pro Gln Asp Lys
1               5                   10                  15

Leu Glu Glu Leu Lys Lys Ile Asn Asp Ala Val Lys Lys Thr Lys Asn
            20                  25                  30

Phe Ser Lys Tyr Leu Ile Asp Leu Arg Lys Leu Phe Gln Ile Asp Glu
        35                  40                  45

Val Gln Val Thr Ser Glu Ser Lys Leu Phe Leu Ala Gly Phe Leu Glu
    50                  55                  60

Gly Glu Ala Ser Leu Asn Ile Ser Thr Lys Lys Leu Ala Thr Ser Lys
65                  70                  75                  80

Phe Gly Leu Val Val Asp Pro Glu Phe Asn Val Thr Gln His Val Asn
                85                  90                  95

Gly Val Lys Val Leu Tyr Leu Ala Leu Glu Val Phe Lys Thr Gly Arg
            100                 105                 110

Ile Arg His Lys Ser Gly Ser Asn Ala Thr Leu Val Leu Thr Ile Asp
        115                 120                 125

Asn Arg Gln Ser Leu Glu Glu Lys Val Ile Pro Phe Tyr Glu Gln Tyr
    130                 135                 140

Val Val Ala Phe Ser Ser Pro Glu Lys Val Lys Arg Val Ala Asn Phe
145                 150                 155                 160

Lys Ala Leu Leu Glu Leu Phe Asn Asn Asp Ala His Gln Asp Leu Glu
                165                 170                 175

Gln Leu Val Asn Lys Ile Leu Pro Ile Trp Asp Gln Met Arg Lys Gln
            180                 185                 190

Gln Gly Gln Ser Asn Glu Gly Phe Pro Asn Leu Glu Ala Ala Gln Asp
        195                 200                 205

Phe Ala Arg Asn Tyr Lys Lys Gly Ile Lys
    210                 215

<210> SEQ ID NO 4
<211> LENGTH: 194
<212> TYPE: PRT
<213> ORGANISM: Desulfurococcus mobilis

<400> SEQUENCE: 4

Met His Asn Asn Glu Asn Val Ser Gly Ile Ser Ala Tyr Leu Leu Gly
1               5                   10                  15

Leu Ile Ile Gly Asp Gly Gly Leu Tyr Lys Leu Lys Tyr Lys Gly Asn
            20                  25                  30

Arg Ser Glu Tyr Arg Val Val Ile Thr Gln Lys Ser Glu Asn Leu Ile
        35                  40                  45

Lys Gln His Ile Ala Pro Leu Met Gln Phe Leu Ile Asp Glu Leu Asn
    50                  55                  60

Val Lys Ser Lys Ile Gln Ile Val Lys Gly Asp Thr Arg Tyr Glu Leu
65                  70                  75                  80

Arg Val Ser Ser Lys Lys Leu Tyr Tyr Phe Ala Asn Met Leu Glu
                85                  90                  95

Arg Ile Arg Leu Phe Asn Met Arg Glu Gln Ile Ala Phe Ile Lys Gly
            100                 105                 110

Leu Tyr Val Ala Glu Gly Asp Lys Thr Leu Lys Arg Leu Arg Ile Trp
        115                 120                 125

Asn Lys Asn Lys Ala Leu Leu Glu Ile Val Ser Arg Trp Leu Asn Asn
    130                 135                 140

Leu Gly Val Arg Asn Thr Ile His Leu Asp Asp His Arg His Gly Val
145                 150                 155                 160
```

-continued

Tyr Val Leu Asn Ile Ser Leu Arg Asp Arg Ile Lys Phe Val His Thr
            165                 170                 175

Ile Leu Ser Ser His Leu Asn Pro Leu Pro Glu Arg Ala Gly Gly
        180                 185                 190

Tyr Thr

<210> SEQ ID NO 5
<211> LENGTH: 235
<212> TYPE: PRT
<213> ORGANISM: Saccharomyces cerevisiae

<400> SEQUENCE: 5

Met Lys Asn Ile Lys Lys Asn Gln Val Met Asn Leu Gly Pro Asn Ser
1               5                   10                  15

Lys Leu Leu Lys Glu Tyr Lys Ser Gln Leu Ile Glu Leu Asn Ile Glu
            20                  25                  30

Gln Phe Glu Ala Gly Ile Gly Leu Ile Leu Gly Asp Ala Tyr Ile Arg
        35                  40                  45

Ser Arg Asp Glu Gly Lys Thr Tyr Cys Met Gln Phe Glu Trp Lys Asn
50                  55                  60

Lys Ala Tyr Met Asp His Val Cys Leu Leu Tyr Asp Gln Trp Val Leu
65                  70                  75                  80

Ser Pro Pro His Lys Lys Glu Arg Val Asn His Leu Gly Asn Leu Val
                85                  90                  95

Ile Thr Trp Gly Ala Gln Thr Phe Lys His Gln Ala Phe Asn Lys Leu
            100                 105                 110

Ala Asn Leu Phe Ile Val Asn Asn Lys Lys Thr Ile Pro Asn Asn Leu
        115                 120                 125

Val Glu Asn Tyr Leu Thr Pro Met Ser Leu Ala Tyr Trp Phe Met Asp
130                 135                 140

Asp Gly Gly Lys Trp Asp Tyr Asn Lys Asn Ser Thr Asn Lys Ser Ile
145                 150                 155                 160

Val Leu Asn Thr Gln Ser Phe Thr Phe Glu Glu Val Glu Tyr Leu Val
                165                 170                 175

Lys Gly Leu Arg Asn Lys Phe Gln Leu Asn Cys Tyr Val Lys Ile Asn
            180                 185                 190

Lys Asn Lys Pro Ile Ile Tyr Ile Asp Ser Met Ser Tyr Leu Ile Phe
        195                 200                 205

Tyr Asn Leu Ile Lys Pro Tyr Leu Ile Pro Gln Met Met Tyr Lys Leu
210                 215                 220

Pro Asn Thr Ile Ser Ser Glu Thr Phe Leu Lys
225                 230                 235

<210> SEQ ID NO 6
<211> LENGTH: 254
<212> TYPE: PRT
<213> ORGANISM: Emericella nidulans

<400> SEQUENCE: 6

Met Ser Asp Leu Thr Tyr Ala Tyr Leu Val Gly Leu Phe Glu Gly Asp
1               5                   10                  15

Gly Tyr Phe Ser Ile Thr Lys Lys Gly Lys Tyr Leu Thr Tyr Glu Leu
            20                  25                  30

Gly Ile Glu Leu Ser Ile Lys Asp Val Gln Leu Ile Tyr Lys Ile Lys
        35                  40                  45

Lys Ile Leu Gly Ile Gly Ile Val Ser Phe Arg Lys Ile Asn Glu Ile
50                  55                  60

-continued

```
Glu Met Val Ala Leu Arg Ile Arg Asp Lys Asn His Leu Lys Ser Phe
 65                  70                  75                  80

Ile Leu Pro Ile Phe Glu Lys Tyr Pro Met Phe Ser Asn Lys Gln Tyr
                 85                  90                  95

Asp Tyr Leu Arg Phe Arg Asn Ala Leu Leu Ser Gly Ile Ile Ser Leu
            100                 105                 110

Glu Asp Leu Pro Asp Tyr Thr Arg Ser Asp Glu Pro Leu Asn Ser Ile
        115                 120                 125

Glu Ser Ile Ile Asn Thr Ser Tyr Phe Ser Ala Trp Leu Val Gly Phe
    130                 135                 140

Ile Glu Ala Glu Gly Cys Phe Ser Val Tyr Lys Leu Asn Lys Asp Asp
145                 150                 155                 160

Asp Tyr Leu Ile Ala Ser Phe Asp Ile Ala Gln Arg Asp Gly Asp Ile
                165                 170                 175

Leu Ile Ser Ala Ile Arg Lys Tyr Leu Ser Phe Thr Thr Lys Val Tyr
            180                 185                 190

Leu Asp Lys Thr Asn Cys Ser Lys Leu Lys Val Thr Ser Val Arg Ser
        195                 200                 205

Val Glu Asn Ile Ile Lys Phe Leu Gln Asn Ala Pro Val Lys Leu Leu
    210                 215                 220

Gly Asn Lys Lys Leu Gln Tyr Leu Leu Trp Leu Lys Gln Leu Arg Lys
225                 230                 235                 240

Ile Ser Arg Tyr Ser Glu Lys Ile Lys Ile Pro Ser Asn Tyr
                245                 250
```

<210> SEQ ID NO 7
<211> LENGTH: 9
<212> TYPE: DNA
<213> ORGANISM: Chlamydomonas reinhardtii

<400> SEQUENCE: 7 gaaactgtc                                                                 9

<210> SEQ ID NO 8
<211> LENGTH: 9
<212> TYPE: DNA
<213> ORGANISM: Chlamydomonas reinhardtii

<400> SEQUENCE: 8 gacagtttc                                                                 9

<210> SEQ ID NO 9
<211> LENGTH: 9
<212> TYPE: DNA
<213> ORGANISM: Chlamydomonas reinhardtii

<400> SEQUENCE: 9 caaaacgtc                                                                 9

<210> SEQ ID NO 10
<211> LENGTH: 9
<212> TYPE: DNA
<213> ORGANISM: Chlamydomonas reinhardtii

<400> SEQUENCE: 10 gacgttttg                                                                 9

<210> SEQ ID NO 11
<211> LENGTH: 9

```
<212> TYPE: DNA
<213> ORGANISM: Monomastix sp.

<400> SEQUENCE: 11 cagaacgtc                                                              9

<210> SEQ ID NO 12
<211> LENGTH: 9
<212> TYPE: DNA
<213> ORGANISM: Monomastix sp.

<400> SEQUENCE: 12 gacgttctg                                                              9

<210> SEQ ID NO 13
<211> LENGTH: 9
<212> TYPE: DNA
<213> ORGANISM: Monomastix sp.

<400> SEQUENCE: 13 ggaactgtc                                                              9

<210> SEQ ID NO 14
<211> LENGTH: 9
<212> TYPE: DNA
<213> ORGANISM: Monomastix sp.

<400> SEQUENCE: 14 gacagttcc                                                              9

<210> SEQ ID NO 15
<211> LENGTH: 9
<212> TYPE: DNA
<213> ORGANISM: Chlamydomonas moewusii

<400> SEQUENCE: 15 ataacggtc                                                              9

<210> SEQ ID NO 16
<211> LENGTH: 9
<212> TYPE: DNA
<213> ORGANISM: Chlamydomonas moewusii

<400> SEQUENCE: 16 gaccgttat                                                              9

<210> SEQ ID NO 17
<211> LENGTH: 9
<212> TYPE: DNA
<213> ORGANISM: Chlamydomonas moewusii

<400> SEQUENCE: 17 ttcgctacc                                                              9

<210> SEQ ID NO 18
<211> LENGTH: 9
<212> TYPE: DNA
<213> ORGANISM: Chlamydomonas moewusii

<400> SEQUENCE: 18 ggtagcgaa                                                              9

<210> SEQ ID NO 19
<211> LENGTH: 5
```

```
<212> TYPE: DNA
<213> ORGANISM: Saccharomyces cerevisiae

<400> SEQUENCE: 19 taggg                                                                    5

<210> SEQ ID NO 20
<211> LENGTH: 5
<212> TYPE: DNA
<213> ORGANISM: Saccharomyces cerevisiae

<400> SEQUENCE: 20 cccta                                                                    5

<210> SEQ ID NO 21
<211> LENGTH: 9
<212> TYPE: DNA
<213> ORGANISM: Saccharomyces cerevisiae

<400> SEQUENCE: 21 taatgggac                                                                9

<210> SEQ ID NO 22
<211> LENGTH: 9
<212> TYPE: DNA
<213> ORGANISM: Saccharomyces cerevisiae

<400> SEQUENCE: 22 gtcccatta                                                                9

<210> SEQ ID NO 23
<211> LENGTH: 8
<212> TYPE: DNA
<213> ORGANISM: Desulfurococcus mobilis

<400> SEQUENCE: 23 gccggaac                                                                 8

<210> SEQ ID NO 24
<211> LENGTH: 8
<212> TYPE: DNA
<213> ORGANISM: Desulfurococcus mobilis

<400> SEQUENCE: 24 gttccggc                                                                 8

<210> SEQ ID NO 25
<211> LENGTH: 7
<212> TYPE: DNA
<213> ORGANISM: Desulfurococcus mobilis

<400> SEQUENCE: 25 aacggcc                                                                  7

<210> SEQ ID NO 26
<211> LENGTH: 7
<212> TYPE: DNA
<213> ORGANISM: Desulfurococcus mobilis

<400> SEQUENCE: 26 ggccgtt                                                                  7

<210> SEQ ID NO 27
<211> LENGTH: 8
```

```
<212> TYPE: DNA
<213> ORGANISM: Emericella nidulans

<400> SEQUENCE: 27 tttacaga                                                                   8

<210> SEQ ID NO 28
<211> LENGTH: 8
<212> TYPE: DNA
<213> ORGANISM: Emericella nidulans

<400> SEQUENCE: 28 tctgtaaa                                                                   8

<210> SEQ ID NO 29
<211> LENGTH: 9
<212> TYPE: DNA
<213> ORGANISM: Emericella nidulans

<400> SEQUENCE: 29 ctgaggagg                                                                  9

<210> SEQ ID NO 30
<211> LENGTH: 9
<212> TYPE: DNA
<213> ORGANISM: Emericella nidulans

<400> SEQUENCE: 30 cctcctcag                                                                  9

<210> SEQ ID NO 31
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31
```

Met Asn Thr Lys Tyr Asn Lys Glu Phe Leu Leu Tyr Leu Ala Gly Phe
1               5                   10                  15

Val Asp Gly Asp Gly Ser Ile Lys Ala Gln Ile Lys Pro Glu Gln Asn
            20                  25                  30

Arg Lys Phe Lys His Arg Leu Glu Leu Thr Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Tyr Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
aggcatctca ttagagatgc ct                                            22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aggcatctct aatgagatgc ct                                            22

<210> SEQ ID NO 34
<211> LENGTH: 22
<212> TYPE: DNA
<213> ORGANISM: Chlamydomonas reinhardtii

<400> SEQUENCE: 34
gaaactgtct cacgacgttt tg                                            22

<210> SEQ ID NO 35
<211> LENGTH: 22
<212> TYPE: DNA
<213> ORGANISM: Chlamydomonas reinhardtii

<400> SEQUENCE: 35
caaaacgtcg tgagacagtt tc                                            22

<210> SEQ ID NO 36
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Asp Pro Arg Gln Cys
            20                  25                  30

Arg Lys Phe Lys His Glu Leu Arg Leu Arg Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

```
Val Asp Gln Ile Ala Ala Leu Asn Asp Ser Lys Thr Arg Lys Thr Thr
        130                 135                 140

Ser Glu Thr Val Arg Ala Val Leu Asp Ser Leu Ser Glu Lys Lys Lys
145                 150                 155                 160

Ser Ser Pro

<210> SEQ ID NO 37
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Glu Gln Ser
            20                  25                  30

Tyr Lys Phe Lys His Arg Leu Arg Leu Glu Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro

<210> SEQ ID NO 38
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38 tgcggtgtc                                                                9

<210> SEQ ID NO 39
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39 gacaccgca                                                                9

<210> SEQ ID NO 40
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(13)
<223> OTHER INFORMATION: a, c, t, g, u, unknown or other

<400> SEQUENCE: 40
tgcggtgtcn nnngacaccg ca                                              22

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(13)
<223> OTHER INFORMATION: a, c, t, g, u, unknown or other

<400> SEQUENCE: 41
tgcggtgtcn nnngacaccg ca                                              22

<210> SEQ ID NO 42
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42 caggctgtc                                                              9

<210> SEQ ID NO 43
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43 gacagcctg                                                              9

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(13)
<223> OTHER INFORMATION: a, c, t, g, u, unknown or other

<400> SEQUENCE: 44
caggctgtcn nnngacagcc tg                                              22

<210> SEQ ID NO 45
<211> LENGTH: 22
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(13)
<223> OTHER INFORMATION: a, c, t, g, u, unknown or other

<400> SEQUENCE: 45
caggctgtcn nnngacagcc tg                                              22

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tgcggtgtca ttagacagcc tg                                              22

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
caggctgtct aatgacaccg ca                                              22

<210> SEQ ID NO 48
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48
```

Met Asn Thr Lys Tyr Asn Lys Glu Phe Leu Tyr Leu Ala Gly Phe
1               5                   10                  15

Val Asp Gly Asp Gly Ser Ile Ile Ala Gln Ile Asp Pro Arg Gln Cys
            20                  25                  30

Arg Lys Phe Lys His Glu Leu Arg Leu Arg Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Met Leu Glu
                85                  90                  95

Arg Ile Arg Leu Phe Asn Met Arg Glu Phe Leu Leu Tyr Leu Ala Gly
            100                 105                 110

Phe Val Asp Gly Asp Gly Ser Ile Ile Ala Gln Ile Lys Pro Glu Gln
        115                 120                 125

Ser Tyr Lys Phe Lys His Arg Leu Arg Leu Glu Phe Gln Val Thr Gln
    130                 135                 140

Lys Thr Gln Arg Arg Trp Phe Leu Asp Lys Leu Val Asp Glu Ile Gly
145                 150                 155                 160

Val Gly Tyr Val Arg Asp Arg Gly Ser Val Ser Asp Tyr Ile Leu Ser

```
                        165                 170                 175
Glu Ile Lys Pro Leu His Asn Phe Leu Thr Gln Leu Gln Pro Phe Leu
            180                 185                 190

Lys Leu Lys Gln Lys Gln Ala Asn Leu Val Leu Lys Ile Ile Trp Arg
            195                 200                 205

Leu Pro Ser Ala Lys Glu Ser Pro Asp Lys Phe Leu Glu Val Cys Thr
            210                 215                 220

Trp Val Asp Gln Ile Ala Ala Leu Asn Asp Ser Lys Thr Arg Lys Thr
225                 230                 235                 240

Thr Ser Glu Thr Val Arg Ala Val Leu Asp Ser Leu Ser Glu Lys Lys
            245                 250                 255

Lys Ser Ser Pro
            260

<210> SEQ ID NO 49
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Glu Gln Ser
            20                  25                  30

Tyr Lys Phe Lys His Arg Leu Arg Leu Glu Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Met Leu Glu
                85                  90                  95

Arg Ile Arg Leu Phe Asn Met Arg Glu Phe Leu Leu Tyr Leu Ala Gly
            100                 105                 110

Phe Val Asp Gly Asp Gly Ser Ile Ile Ala Gln Ile Asp Pro Arg Gln
            115                 120                 125

Cys Arg Lys Phe Lys His Glu Leu Arg Leu Arg Phe Gln Val Thr Gln
        130                 135                 140

Lys Thr Gln Arg Arg Trp Phe Leu Asp Lys Leu Val Asp Glu Ile Gly
145                 150                 155                 160

Val Gly Tyr Val Arg Asp Arg Gly Ser Val Ser Asp Tyr Ile Leu Ser
                165                 170                 175

Glu Ile Lys Pro Leu His Asn Phe Leu Thr Gln Leu Gln Pro Phe Leu
            180                 185                 190

Lys Leu Lys Gln Lys Gln Ala Asn Leu Val Leu Lys Ile Ile Trp Arg
            195                 200                 205

Leu Pro Ser Ala Lys Glu Ser Pro Asp Lys Phe Leu Glu Val Cys Thr
            210                 215                 220

Trp Val Asp Gln Ile Ala Ala Leu Asn Asp Ser Lys Thr Arg Lys Thr
225                 230                 235                 240

Thr Ser Glu Thr Val Arg Ala Val Leu Asp Ser Leu Ser Glu Lys Lys
            245                 250                 255

Lys Ser Ser Pro
```

<210> SEQ ID NO 50
<211> LENGTH: 334
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Asp Pro Arg Gln Cys
            20                  25                  30

Arg Lys Phe Lys His Glu Leu Arg Leu Arg Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Gly Ser Ser Gly Ser Ser Gly Ser Ser
145                 150                 155                 160

Gly Ser Ser Gly Ser Ser Gly Ser Ser Gly Ser Ser Gly Ser Ser Gly
                165                 170                 175

Ser Ser Gly Phe Leu Leu Tyr Leu Ala Gly Phe Val Asp Gly Asp Gly
            180                 185                 190

Ser Ile Ile Ala Gln Ile Lys Pro Glu Gln Ser Tyr Lys Phe Lys His
        195                 200                 205

Arg Leu Arg Leu Glu Phe Gln Val Thr Gln Lys Thr Gln Arg Arg Trp
    210                 215                 220

Phe Leu Asp Lys Leu Val Asp Glu Ile Gly Val Gly Tyr Val Arg Asp
225                 230                 235                 240

Arg Gly Ser Val Ser Asp Tyr Ile Leu Ser Glu Ile Lys Pro Leu His
                245                 250                 255

Asn Phe Leu Thr Gln Leu Gln Pro Phe Leu Lys Leu Lys Gln Lys Gln
            260                 265                 270

Ala Asn Leu Val Leu Lys Ile Ile Trp Arg Leu Pro Ser Ala Lys Glu
        275                 280                 285

Ser Pro Asp Lys Phe Leu Glu Val Cys Thr Trp Val Asp Gln Ile Ala
    290                 295                 300

Ala Leu Asn Asp Ser Lys Thr Arg Lys Thr Thr Ser Glu Thr Val Arg
305                 310                 315                 320

Ala Val Leu Asp Ser Leu Ser Glu Lys Lys Ser Ser Pro
                325                 330

<210> SEQ ID NO 51
<211> LENGTH: 350
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 51

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Asp Pro Arg Gln Cys
            20                  25                  30

Arg Lys Phe Lys His Glu Leu Arg Leu Arg Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ala Ser Ser
                165                 170                 175

Ser Pro Gly Ser Gly Ile Ser Glu Ala Leu Arg Ala Gly Ala Thr Lys
            180                 185                 190

Ser Lys Glu Phe Leu Leu Tyr Leu Ala Gly Phe Val Asp Gly Asp Gly
        195                 200                 205

Ser Ile Ile Ala Gln Ile Lys Pro Glu Gln Ser Tyr Lys Phe Lys His
    210                 215                 220

Arg Leu Arg Leu Glu Phe Gln Val Thr Gln Lys Thr Gln Arg Arg Trp
225                 230                 235                 240

Phe Leu Asp Lys Leu Val Asp Glu Ile Gly Val Gly Tyr Val Arg Asp
                245                 250                 255

Arg Gly Ser Val Ser Asp Tyr Ile Leu Ser Glu Ile Lys Pro Leu His
            260                 265                 270

Asn Phe Leu Thr Gln Leu Gln Pro Phe Leu Lys Leu Lys Gln Lys Gln
        275                 280                 285

Ala Asn Leu Val Leu Lys Ile Ile Trp Arg Leu Pro Ser Ala Lys Glu
    290                 295                 300

Ser Pro Asp Lys Phe Leu Glu Val Cys Thr Trp Val Asp Gln Ile Ala
305                 310                 315                 320

Ala Leu Asn Asp Ser Lys Thr Arg Lys Thr Thr Ser Glu Thr Val Arg
                325                 330                 335

Ala Val Leu Asp Ser Leu Ser Glu Lys Lys Ser Ser Pro
            340                 345                 350

<210> SEQ ID NO 52
<211> LENGTH: 373
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

```
Met Thr Thr Lys Asn Thr Leu Gln Pro Thr Glu Ala Ala Tyr Ile Ala
1               5                   10                  15

Gly Phe Leu Asp Gly Asp Gly Ser Ile Tyr Ala Lys Leu Ile Pro Arg
            20                  25                  30

Pro Asp Tyr Lys Asp Ile Lys Tyr Gln Val Ser Leu Ala Ile Ser Phe
        35                  40                  45

Ile Gln Arg Lys Asp Lys Phe Pro Tyr Leu Gln Asp Ile Tyr Asp Gln
    50                  55                  60

Leu Gly Lys Arg Gly Asn Leu Arg Lys Asp Arg Gly Asp Gly Ile Ala
65                  70                  75                  80

Asp Tyr Thr Ile Ile Gly Ser Thr His Leu Ser Ile Ile Leu Pro Asp
                85                  90                  95

Leu Val Pro Tyr Leu Arg Ile Lys Lys Gln Ala Asn Arg Ile Leu
            100                 105                 110

His Ile Ile Asn Leu Tyr Pro Gln Ala Gln Lys Asn Pro Ser Lys Phe
        115                 120                 125

Leu Asp Leu Val Lys Ile Val Asp Asp Val Gln Asn Leu Asn Lys Arg
    130                 135                 140

Ala Asp Glu Leu Lys Ser Thr Asn Tyr Asp Arg Leu Leu Glu Glu Phe
145                 150                 155                 160

Leu Lys Ala Gly Lys Ile Gly Gly Ala Ser Pro Ser Gln Ala Ser Ser
                165                 170                 175

Ala Ala Ser Ser Ala Ser Ser Ala Ser Ser Pro Gly Ser Gly Pro
            180                 185                 190

Ser Glu Ala Leu Arg Ala Ala Ser Ser Phe Ala Ser Lys Pro Gly Ser
    195                 200                 205

Thr Leu Gln Pro Thr Glu Ala Ala Tyr Ile Ala Gly Phe Leu Asp Gly
    210                 215                 220

Asp Gly Ser Ile Tyr Ala Lys Leu Ile Pro Arg Pro Asp Tyr Lys Asp
225                 230                 235                 240

Ile Lys Tyr Gln Val Ser Leu Ala Ile Ser Phe Ile Gln Arg Lys Asp
                245                 250                 255

Lys Phe Pro Tyr Leu Gln Asp Ile Tyr Asp Gln Leu Gly Lys Arg Gly
                260                 265                 270

Asn Leu Arg Lys Asp Arg Gly Asp Gly Ile Ala Asp Tyr Thr Ile Ile
            275                 280                 285

Gly Ser Thr His Leu Ser Ile Ile Leu Pro Asp Leu Val Pro Tyr Leu
        290                 295                 300

Arg Ile Lys Lys Lys Gln Ala Asn Arg Ile Leu His Ile Ile Asn Leu
305                 310                 315                 320

Tyr Pro Gln Ala Gln Lys Asn Pro Ser Lys Phe Leu Asp Leu Val Lys
                325                 330                 335

Ile Val Asp Asp Val Gln Asn Leu Asn Lys Arg Ala Asp Glu Leu Lys
            340                 345                 350

Ser Thr Asn Tyr Asp Arg Leu Leu Glu Glu Phe Leu Lys Ala Gly Lys
    355                 360                 365

Ile Glu Ser Ser Pro
    370
```

<210> SEQ ID NO 53
<211> LENGTH: 22
<212> TYPE: DNA

```
<213> ORGANISM: Monomastix sp.

<400> SEQUENCE: 53
ggaactgtct cacgacgttc tg                                              22

<210> SEQ ID NO 54
<211> LENGTH: 22
<212> TYPE: DNA
<213> ORGANISM: Monomastix sp.

<400> SEQUENCE: 54
cagaacgtcg tgagacagtt cc                                              22

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Ala Gly Leu Ile Asp Ala Asp Gly
1               5

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(13)
<223> OTHER INFORMATION: a, c, t, g, u, unknown or other

<400> SEQUENCE: 56
tgcggtgtcn nngacagcc tg                                               22

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(13)
<223> OTHER INFORMATION: a, c, t, g, u, unknown or other

<400> SEQUENCE: 57
caggctgtcn nngacaccg ca                                               22

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser Gly Gly Ser
1

<210> SEQ ID NO 59
```

```
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Ser Ser Gly Ser Ser Gly Ser Ser Gly Ser Ser Gly Ser Ser Gly
1               5                   10                  15

Ser Ser Gly Ser Ser Gly
            20

<210> SEQ ID NO 60
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Ser Ser Gly Ser Ser Gly Ser Ser Gly Ser Ser Gly Ser Ser Gly
1               5                   10                  15

Ser Ser Gly Ser Ser Gly Ser Ser Gly
            20                  25

<210> SEQ ID NO 61
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Ser Ser Gly Ser Ser Gly Ser Ser Gly Ser Ser Gly Ser Ser Gly
1               5                   10                  15

Ser Ser Gly Ser Ser Gly Ser Ser Gly Ser Ser Gly
            20                  25

<210> SEQ ID NO 62
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gly Ser Ser Gly Ser Ser Gly Ser Ser Gly Ser Ser Gly Ser Ser Gly
1               5                   10                  15

Ser Ser Gly Ser Ser Gly Ser Ser Gly Ser Ser Gly Ser Ser Gly
            20                  25                  30

<210> SEQ ID NO 63
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gly Ser Ser Gly Ser Ser Gly Ser Ser Gly Ser Ser Gly Ser Ser Gly
1               5                   10                  15
```

Ser Ser Gly Ser Ser Gly Ser Ser Gly Ser Ser Gly Ser
            20                  25                  30

Ser Gly

<210> SEQ ID NO 64
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Ser Ser Gly Ser Ser Gly Ser Ser Gly Ser Ser Gly Ser Ser Gly
1               5                   10                  15

Ser Ser Gly Ser Ser Gly Ser Ser Gly Ser Ser Gly Gly
            20                  25

<210> SEQ ID NO 65
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gly Ser Ser Gly Ser Ser Gly Ser Ser Gly Ser Ser Gly Ser Ser Gly
1               5                   10                  15

Ser Ser Gly Ser Ser Gly Ser Ser Gly Ser Ser Gly Ser Gly
            20                  25                  30

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Val Leu Asp Ser Pro Gly Ser Val
1               5

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ser Gln Ala Ser Ser Ala Ala Ser Ser Ala Ser Ser
1               5                   10

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Leu Ser Pro Ser Gln Ala
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Ser Ser Ser Pro Gly Ser Gly Ile
1               5

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Ser Ser Ser
1

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Pro Gly Ser Gly Ile
1               5

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ile Ser Glu Ala Leu Arg
1               5

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Glu Ala Leu Arg Ala
1               5

<210> SEQ ID NO 74
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 74

Ala Ser Ser Ala
1

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Leu Arg Ala Gly Ala
1               5

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Thr Lys Ser Lys Glu Phe
1               5

<210> SEQ ID NO 77
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Ser Leu Pro Gly Ser Val Gly Gly Leu Ser Pro Ser Gln Ala Ser Ser
1               5                   10                  15

Ala Ala Ser Ser Ala Ser Ser Ser Pro Gly Ser Gly Ile Ser Glu Ala
            20                  25                  30

Leu Arg Ala Gly Ala Thr Lys Ser
        35                  40

<210> SEQ ID NO 78
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Ser Leu Pro Gly Ser Val Gly Gly Leu Ser Pro Ser Gln Ala Ser Ser
1               5                   10                  15

Ala Ala Ser Ser Ala Ser Ser Ser Pro Gly Ser Gly Ile Ser Glu Ala
            20                  25                  30

Leu Arg Ala Gly Gly Ala Thr Lys Ser
        35                  40

<210> SEQ ID NO 79
<211> LENGTH: 42
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 79

Ser Leu Pro Gly Ser Val Gly Gly Leu Ser Pro Ser Gln Ala Ser Ser
1               5                   10                  15

Ala Ala Ser Ser Ala Ser Ser Pro Gly Ser Gly Ile Ser Glu Ala
            20                  25                  30

Leu Arg Ala Ala Gly Gly Ala Thr Lys Ser
        35                  40

<210> SEQ ID NO 80
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Ser Leu Pro Gly Ser Val Gly Gly Leu Ser Pro Ser Gln Ala Ser Ser
1               5                   10                  15

Ala Ala Ser Ser Ala Ser Ser Pro Gly Ser Gly Ile Ser Glu Ala
            20                  25                  30

Leu Arg Ala Ala Ser Gly Gly Ala Thr Lys Ser
        35                  40

<210> SEQ ID NO 81
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Ser Leu Pro Gly Ser Val Gly Gly Leu Ser Pro Ser Gln Ala Ser Ser
1               5                   10                  15

Ala Ala Ser Ser Ala Ser Ser Pro Gly Ser Gly Ile Ser Glu Ala
            20                  25                  30

Leu Arg Ala Ala Ser Ser Gly Gly Ala Thr Lys Ser
        35                  40

<210> SEQ ID NO 82
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Ser Leu Pro Gly Ser Val Gly Gly Leu Ser Pro Ser Gln Ala Ser Ser
1               5                   10                  15

Ala Ala Ser Ser Ala Ser Ser Pro Gly Ser Gly Ile Ser Glu Ala
            20                  25                  30

Leu Arg Ala Ala Ser Ser Ala Gly Gly Ala Thr Lys Ser
        35                  40                  45

<210> SEQ ID NO 83
<211> LENGTH: 41
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

Ser Leu Pro Gly Ser Val Gly Gly Leu Ser Pro Ser Gln Ala Ser Ser
1               5                   10                  15

Ala Ala Ser Ser Ala Ser Ser Pro Gly Ser Gly Ile Ser Glu Ala
            20                  25                  30

Leu Arg Ala Gly Ala Thr Lys Glu Phe
        35                  40

<210> SEQ ID NO 84
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Ser Leu Pro Gly Ser Val Gly Gly Ile Ser Pro Ser Gln Ala Ser Ser
1               5                   10                  15

Ala Ala Ser Ser Ala Ser Ser Pro Gly Ser Gly Thr Ser Glu Ala
            20                  25                  30

Pro Arg Ala Gly Ala Thr Lys Glu Phe
        35                  40

<210> SEQ ID NO 85
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Ser Leu Pro Gly Ser Val Gly Gly Leu Ser Pro Ser Gln Ala Ser Ser
1               5                   10                  15

Ala Ala Ser Ser Ala Ser Ser Pro Gly Ser Gly Thr Ser Glu Ala
            20                  25                  30

Thr Arg Ala Gly Ala Thr Lys Glu Phe
        35                  40

<210> SEQ ID NO 86
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Ser Leu Pro Gly Ser Leu Gly Gly Leu Ser Pro Ser Gln Ala Ser Ser
1               5                   10                  15

Ala Ala Ser Ser Ala Ser Ser Pro Gly Ser Gly Pro Ser Glu Ala
            20                  25                  30

Leu Arg Ala Gly Ala Thr Lys Glu Phe
        35                  40

<210> SEQ ID NO 87
<211> LENGTH: 41
<212> TYPE: PRT
<213> ORGANISM: Artificial Sequence
<220> FEATURE:
<223> OTHER INFORMATION: Description of Artificial Sequence: Synthetic -continued

```
      polypeptide

<400> SEQUENCE: 87

Ser Leu Pro Gly Ser Val Gly Gly Val Ser Pro Ser Gln Ala Ser Ser
1               5                   10                  15

Ala Ala Ser Ser Ala Ser Ser Ser Pro Gly Ser Gly Val Ser Glu Ala
            20                  25                  30

Ser Arg Ala Gly Ala Thr Lys Glu Phe
        35                  40

<210> SEQ ID NO 88
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Ser Leu Pro Gly Ser Val Gly Gly Leu Ser Pro Ser Gln Ala Ser Ser
1               5                   10                  15

Ala Ala Ser Ser Ala Ser Ser Ser Pro Gly Ser Gly Leu Ser Glu Ala
            20                  25                  30

Leu Arg Ala Gly Ala Thr Lys Glu Phe
        35                  40

<210> SEQ ID NO 89
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Ser Leu Pro Gly Ser Leu Gly Gly Ile Ser Pro Ser Gln Ala Ser Ser
1               5                   10                  15

Ala Ala Ser Ser Ala Ser Ser Ser Pro Gly Ser Gly Ser Ser Glu Ala
            20                  25                  30

Ser Arg Ala Gly Ala Thr Lys Glu Phe
        35                  40

<210> SEQ ID NO 90
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Ser Pro Gly Ser Val Gly Gly Val Ser Pro Ser Gln Ala Ser Ser Ala
1               5                   10                  15

Ala Ser Ser Ala Ser Ser Ser Pro Gly Ser Gly Ile Ser Glu Ala Thr
            20                  25                  30

Arg Ala Gly Ala Thr Lys Glu Phe
        35                  40

<210> SEQ ID NO 91
<211> LENGTH: 37
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 91

Ser Leu Pro Gly Ser Leu Gly Gly Val Ser Pro Ser Gln Ala Ser Ser
1               5                   10                  15

Ala Ala Ser Ser Pro Gly Ser Gly Thr Ser Glu Ala Pro Arg Ala Gly
            20                  25                  30

Ala Thr Lys Glu Phe
        35

<210> SEQ ID NO 92
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Ser Leu Pro Gly Ser Val Gly Gly Leu Ser Pro Ser Gln Ala Ser Ser
1               5                   10                  15

Ala Ala Ser Ser Pro Gly Ser Gly Ile Ser Glu Ala Ile Arg Ala Gly
            20                  25                  30

Ala Thr Lys Glu Phe
        35

<210> SEQ ID NO 93
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Ser Leu Pro Gly Ser Leu Gly Gly Val Ser Pro Ser Gln Ala Ser Ser
1               5                   10                  15

Ala Ala Ser Ser Ala Ser Ser Ala Ala Ser Ser Pro Gly Ser Gly Ala
            20                  25                  30

Ser Glu Ala Ser Arg Ala Gly Ala Thr Lys Glu Phe
        35                  40

<210> SEQ ID NO 94
<211> LENGTH: 6
<212> TYPE: PRT
<213> ORGANISM: Monomastix sp.

<400> SEQUENCE: 94

Leu Gln Pro Thr Glu Ala
1               5

<210> SEQ ID NO 95
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Pro Gly Ser Val Gly Gly Leu Ser Pro Ser Gln Ala Ser Ser Ala Ala
1               5                   10                  15

Ser Ser Ala Ser Ser Ser Pro Gly Ser Gly Ile Ser Glu Ala Leu Arg
            20                  25                  30

```
Ala Gly Ala Thr Lys Ser Ala
        35
```

<210> SEQ ID NO 96
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

```
Pro Gly Ser Val Gly Gly Leu Ser Pro Ser Gln Ala Ser Ala Ala
1               5                   10                  15

Ser Ser Ala Ser Ser Ser Pro Gly Ser Gly Ile Ser Glu Ala Leu Arg
            20                  25                  30

Ala Gly Ala Thr Lys Ser Gly
        35
```

<210> SEQ ID NO 97
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

```
Gly Gly Ala Ser Pro Ser Gln Ala Ser Ser Ala Ala Ser Ser Ala Ser
1               5                   10                  15

Ser Ala Ala Ser Ser Pro Gly Ser Gly Ile Ser Glu Ala Leu Arg Ala
            20                  25                  30

Ala Ser Ser Leu Ala Ser Lys Pro Gly Ser Thr
        35                  40
```

<210> SEQ ID NO 98
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

```
Gly Gly Ala Ser Pro Ser Gln Ala Ser Ser Ala Ala Ser Ser Ala Ser
1               5                   10                  15

Ser Ala Ala Ser Ser Pro Gly Ser Gly Ile Ser Glu Ala Leu Arg Ala
            20                  25                  30

Ala Ser Ser Pro Gly Ser Thr
        35
```

<210> SEQ ID NO 99
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

```
Gly Gly Ala Ser Pro Ser Gln Ala Ser Ser Ala Ala Ser Ser Ala Ser
1               5                   10                  15

Ser Ala Ala Ser Ser Pro Gly Ser Gly Pro Ser Glu Ala Leu Arg Ala
            20                  25                  30
```

```
Ala Ser Ser Phe Ala Ser Lys Pro Gly Ser Thr
         35                  40

<210> SEQ ID NO 100
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Leu Pro Gly Glu
1

<210> SEQ ID NO 101
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Ser Ser Gly Ser Ser Gly Ser Ser Gly Ser Ser Gly
1               5                   10

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Ser Ser Gly Ser Ser Gly Ser Ser Gly Ser Ser Gly Ser Ser Gly
1               5                   10                  15

<210> SEQ ID NO 103
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Asn Ser Leu Pro Gly Ser Val Gly Gly Leu Ser Pro Ser Gln Ala Ser
1               5                   10                  15

Ser Ala Ala Ser Ser Ala Ser Ser Ser Pro Gly Ser Gly
            20                  25

<210> SEQ ID NO 104
<211> LENGTH: 11
<212> TYPE: PRT
<213> ORGANISM: Desulfurococcus mobilis

<400> SEQUENCE: 104

Met Leu Glu Arg Ile Arg Leu Phe Asn Met Arg
1               5                   10

<210> SEQ ID NO 105
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 105
tgcggtgtca ttagacaccg ca                                              22

<210> SEQ ID NO 106
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
tgcggtgtct aatgacaccg ca                                              22

<210> SEQ ID NO 107
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
caggctgtca ttagacagcc tg                                              22

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
caggctgtca ttagacagcc tg                                              22

<210> SEQ ID NO 109
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Val Leu Asp Ser Leu Pro Gly Ser Val Gly Leu Ser Pro Ser Gln
1               5                   10                  15

Ala Ser Ser Ala Ala Ser Ser Ala Ser Ser Ser Pro Gly Ser Gly Ile
            20                  25                  30

Ser Glu Ala Leu Arg Ala Gly Ala Thr Lys Ser Lys Glu Phe
        35                  40                  45

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 110

His His His His His His
1               5
```

RATIONALLY-DESIGNED SINGLE-CHAIN MEGANUCLEASES WITH NON-PALINDROMIC RECOGNITION SEQUENCES

CROSS-REFERENCE TO RELATED APPLICATIONS

This application is a continuation of International Patent Application PCT/US2008/082072, filed Oct. 31, 2008, which claims priority to U.S. Provisional Application No. 61/001, 247, filed Oct. 31, 2007, the entire disclosures of which are incorporated by reference herein.

SEQUENCE LISTING

The instant application contains a Sequence Listing which has been submitted in ASCII format via EFS-Web and is hereby incorporated by reference in its entirety. Said ASCII copy, created on Dec. 20, 2012, is named 2000706-00125US2.txt and is 57,853 bytes in size.

FIELD OF THE INVENTION

The invention relates to the field of molecular biology and recombinant nucleic acid technology. In particular, the invention relates to rationally-designed, non-naturally-occurring meganucleases in which a pair of enzyme subunits having specificity for different recognition sequence half-sites are joined into a single polypeptide to form a functional heterodimer with a non-palindromic recognition sequence. The invention also relates to methods of producing such meganucleases, and methods of producing recombinant nucleic acids and organisms using such meganucleases.

BACKGROUND OF THE INVENTION

Genome engineering requires the ability to insert, delete, substitute and otherwise manipulate specific genetic sequences within a genome, and has numerous therapeutic and biotechnological applications. The development of effective means for genome modification remains a major goal in gene therapy, agrotechnology, and synthetic biology (Porteus et al. (2005), *Nat. Biotechnol.* 23: 967-73; Tzfira et al. (2005), *Trends Biotechnol.* 23: 567-9; McDaniel et al. (2005), *Curr. Opin. Biotechnol.* 16: 476-83). A common method for inserting or modifying a DNA sequence involves introducing a transgenic DNA sequence flanked by sequences homologous to the genomic target and selecting or screening for a successful homologous recombination event. Recombination with the transgenic DNA occurs rarely but can be stimulated by a double-stranded break in the genomic DNA at the target site. Numerous methods have been employed to create DNA double-stranded breaks, including irradiation and chemical treatments. Although these methods efficiently stimulate recombination, the double-stranded breaks are randomly dispersed in the genome, which can be highly mutagenic and toxic. At present, the inability to target gene modifications to unique sites within a chromosomal background is a major impediment to successful genome engineering.

One approach to achieving this goal is stimulating homologous recombination at a double-stranded break in a target locus using a nuclease with specificity for a sequence that is sufficiently large to be present at only a single site within the genome (see, e.g., Porteus et al. (2005), *Nat. Biotechnol.* 23: 967-73). The effectiveness of this strategy has been demonstrated in a variety of organisms using chimeric fusions between an engineered zinc finger DNA-binding domain and the non-specific nuclease domain of the FokI restriction enzyme (Porteus (2006), *Mol. Ther.* 13: 438-46; Wright et al. (2005), *Plant J.* 44: 693-705; Urnov et al. (2005), *Nature* 435: 646-51). Although these artificial zinc finger nucleases stimulate site-specific recombination, they retain residual non-specific cleavage activity resulting from under-regulation of the nuclease domain and frequently cleave at unintended sites (Smith et al. (2000), *Nucleic Acids Res.* 28: 3361-9). Such unintended cleavage can cause mutations and toxicity in the treated organism (Porteus et al. (2005), *Nat. Biotechnol.* 23: 967-73).

A group of naturally-occurring nucleases which recognize 15-40 base-pair cleavage sites commonly found in the genomes of plants and fungi may provide a less toxic genome engineering alternative. Such "meganucleases" or "homing endonucleases" are frequently associated with parasitic DNA elements, such as group I self-splicing introns and inteins. They naturally promote homologous recombination or gene insertion at specific locations in the host genome by producing a double-stranded break in the chromosome, which recruits the cellular DNA-repair machinery (Stoddard (2006), *Q. Rev. Biophys.* 38: 49-95). Meganucleases are commonly grouped into four families: the LAGLIDADG (SEQ ID NO: 55) family, the GIY-YIG family, the His-Cys box family and the HNH family. These families are characterized by structural motifs, which affect catalytic activity and recognition sequence. For instance, members of the LAGLIDADG (SEQ ID NO 55) family are characterized by having either one or two copies of the conserved LAGLIDADG (SEQ ID NO: 55) motif (see Chevalier et al. (2001), *Nucleic Acids Res.* 29(18): 3757-3774). The LAGLIDADG (SEQ ID NO: 55) meganucleases with a single copy of the LAGLIDADG (SEQ ID NO: 55) motif ("mono-LAGLIDADG (SEQ ID NO: 55) meganucleases") form homodimers, whereas members with two copies of the LAGLIDADG (SEQ ID NO: 55) motif ("di-LAGLIDADG (SEQ ID NO: 55) meganucleases") are found as monomers. Mono-LAGLIDADG (SEQ ID NO: 55) meganucleases such as I-CreI, I-CeuI, and I-MsoI recognize and cleave DNA sites that are palindromic or pseudo-palindromic, while di-LAGLIDADG (SEQ ID NO: 55) meganucleases such as I-SceI, I-AniI, and I-DmoI generally recognize DNA sites that are non-palindromic (Stoddard (2006), *Q. Rev. Biophys.* 38: 49-95).

Natural meganucleases from the LAGLIDADG (SEQ ID NO: 55) family have been used to effectively promote site-specific genome modification in plants, yeast, *Drosophila*, mammalian cells and mice, but this approach has been limited to the modification of either homologous genes that conserve the meganuclease recognition sequence (Monnat et al. (1999), *Biochem. Biophys. Res. Common.* 255: 88-93) or to pre-engineered genomes into which a recognition sequence has been introduced (Rouet et al. (1994), *Mol. Cell. Biol.* 14: 8096-106; Chilton et al. (2003), *Plant Physiol.* 133: 956-65; Puchta et al. (1996), *Proc. Natl. Acad. Sci. USA* 93: 5055-60; Rong et al. (2002), *Genes Dev.* 16: 1568-81; Gouble et al. (2006), *J. Gene Med.* 8(5):616-622).

Systematic implementation of nuclease-stimulated gene modification requires the use of genetically engineered enzymes with customized specificities to target DNA breaks to existing sites in a genome and, therefore, there has been great interest in adapting meganucleases to promote gene modifications at medically or biotechnologically relevant sites (Porteus et al. (2005), *Nat. Biotechnol.* 23: 967-73; Sussman et al. (2004), *J. Mol. Biol.* 342: 31-41; Epinat et al. (2003), *Nucleic Acids Res.* 31: 2952-62).

I-CreI is a member of the LAGLIDADG (SEQ ID NO: 55) family which recognizes and cuts a 22 base-pair recognition sequence in the chloroplast chromosome, and which presents an attractive target for meganuclease redesign. The wild-type enzyme is a homodimer in which each monomer makes direct contacts with 9 base pairs in the full-length recognition sequence. Genetic selection techniques have been used to modify the wild-type I-CreI cleavage site preference (Sussman et al. (2004), *J. Mol. Biol.* 342: 31-41; Chames et al. (2005), *Nucleic Acids Res.* 33: e178; Seligman et al. (2002), *Nucleic Acids Res.* 30: 3870-9, Arnould et al. (2006), *J. Mol. Biol.* 355: 443-58, Rosen et al. (2006), *Nucleic Acids Res,* 34: 4791-4800, Arnould et al. (2007). *J. Mol. Biol.* 371: 49-65, WO 2008/010009, WO 2007/093918, WO 2007/093836, WO 2006/097784, WO 2008/059317, WO 2008/059382, WO 2008/102198, WO 2007/060495, WO 2007/049156, WO 2006/097853, WO 2004/067736). More recently, a method of rationally-designing mono-LAGLIDADG (SEQ ID NO: 55) meganucleases was described which is capable of comprehensively redesigning I-CreI and other such meganucleases to target widely-divergent DNA sites, including sites in mammalian, yeast, plant, bacterial, and viral genomes (WO 2007/047859).

A major limitation of using mono-LAGLIDADG (SEQ ID NO:55) meganucleases such as I-CreI for most genetic engineering applications is the fact that these enzymes naturally target palindromic DNA recognition sites. Such lengthy (10-40 bp) palindromic DNA sites are rare in nature and are unlikely to occur by chance in a DNA site of interest. In order to target a non-palindromic DNA site with a mono-LAGLIDADG (SEQ ID NO: 55) meganuclease, one can produce a pair of monomers which recognize the two different half-sites and which heterodimerize to form a meganuclease that cleaves the desired non-palindromic site. Heterodimerization can be achieved either by co-expressing a pair of meganuclease monomers in a host cell or by mixing a pair of purified homodimeric meganucleases in vitro and allowing the subunits to re-associate into heterodimers (Smith et al. (2006), *Nuc. Acids Res.* 34:149-157; Chames et al. (2005), *Nucleic Acids Res.* 33:178-186; WO 2007/047859, WO 2006/097854, WO 2007/057781, WO 2007/049095, WO 2007/034262). Both approaches suffer from two primary limitations: (1) they require the expression of two meganuclease genes to produce the desired heterodimeric species (which complicates gene delivery and in vivo applications) and (2) the result is a mixture of approximately 25% the first homodimer, 50% the heterodimer, and 25% the second homodimer, whereas only the heterodimer is desired. This latter limitation can be overcome to a large extent by genetically engineering the dimerization interfaces of the two meganucleases to promote heterodimerization over homodimerization as described in WO 2007/047859, WO 2008/093249, WO 2008/093152, and Fajardo-Sanchez et al. (2008). *Nucleic Acids Res.* 36:2163-2173. Even so, two meganuclease genes must be expressed and homodimerization is not entirely prevented.

An alternative approach to the formation of meganucleases with non-palindromic recognition sites derived from one or more mono-LAGLIDADG (SEQ ID 55) meganucleases is the production of a single polypeptide which comprises a fusion of the LAGLIDADG (SEQ ID NO: 55) subunits derived from two meganucleases. Two general methods can be applied to produce such a meganuclease.

In the first method, one of the two LAGLIDADG (SEQ ID NO: 55) subunits of a di-LAGLIDADG (SEQ ID NO: 55) meganuclease can be replaced by a LAGLIDADG (SEQ ID NO: 55) subunit from a mono-LAGLIDADG (SEQ ID NO: 55) meganuclease. This approach was demonstrated by replacing the C-terminal subunit of the di-LAGLIDADG (SEQ ID NO: 55) I-DmoI meganuclease with an I-CreI subunit (Epinat et al. (2003), *Nucleic Acids Res.* 31: 2952-62; Chevalier et al. (2002), *Mol. Cell* 10:895-905; WO 2003/078619). The result was a hybrid I-DmoI/I-CreI meganuclease which recognized and cleaved a hybrid DNA site.

In the second method, a pair of mono-LAGLIDADG (SEQ ID NO: 55) subunits can be joined by a peptide linker to create a "single-chain heterodimer meganuclease." One attempt to produce such a single-chain derivative of I-CreI has been reported (Epinat et al. (2003), *Nucleic Acids Res.* 31: 2952-62; WO 2003/078619). However, as discussed herein as well as in Fajardo-Sanchez et al. (2008), *Nucleic Acids Res.* 36:2163-2173, there is now evidence suggesting that this method did not produce a single-chain heterodimer meganuclease in which the covalently joined I-CreI subunits functioned together to recognize and cleave a non-palindromic recognition site.

Therefore, there remains a need in the art for methods for the production of single-chain heterodimer meganucleases derived from mono-LAGLIDADG (SEQ ID NO: 55) enzymes such as I-CreI to recognize and cut non-palindromic DNA sites.

SUMMARY OF THE INVENTION

The present invention is based, in part, upon the development of fusion proteins in which a peptide linker covalently joins two heterologous LAGLIDADG (SEQ ID NO: 55) meganuclease subunits to form a "single-chain heterodimer meganuclease" or "single-chain meganuclease", in which at least the N-terminal subunit is derived from a mono-LAGLIDADG (SEQ ID NO: 55) meganuclease, and in which the subunits function together to preferentially bind to and cleave a non-palindromic DNA recognition site which is a hybrid of the recognition half-sites of the two subunits. In particular, the invention can be used to genetically engineer single-chain meganucleases which recognize non-palindromic DNA sequences that naturally-occurring meganucleases do not recognize. The invention also provides methods that use such meganucleases to produce recombinant nucleic acids and organisms by utilizing the meganucleases to cause recombination of a desired genetic sequence at a limited number of loci within the genome of the organism for, inter alia, genetic engineering, gene therapy, treatment of pathogenic infections, and in vitro applications in diagnostics and research.

Thus, in some embodiments, the invention provides recombinant single-chain meganucleases comprising a pair of covalently joined LAGLIDADG (SEQ ID NO: 55) subunits derived from one or more mono-LAGLIDADG (SEQ ID NO: 55) meganucleases which function together to recognize and cleave a non-palindromic recognition site. In some embodiments, the mono-LAGLIDADG (SEQ ID NO: 55) subunit is derived from a wild-type meganuclease selected from I-CreI, I-MsoI and I-CeuI.

In other embodiments, the invention provides recombinant single-chain meganucleases comprising a pair of mono-LAGLIDADG (SEQ ID NO: 55) subunits in which the N-terminal subunit is derived from a wild-type meganuclease selected from I-CreI, I-MsoI and I-CeuI, and the C-terminal subunit is also derived from a wild-type meganuclease selected from I-CreI, I-MsoI and I-CeuI, but the N-terminal subunit is derived from a wild-type meganuclease of a different species than the C-terminal subunit.

In some embodiments, the invention provides recombinant single-chain meganucleases comprising a pair of LAGL- IDADG (SEQ ID NO: 55) subunits in which the N-terminal subunit is derived from a wild-type meganuclease selected from I-CreI, I-MsoI and I-CeuI, and the C-terminal subunit is derived from a single LAGLIDADG (SEQ ID NO: 55) subunit from a wild-type di-LAGLIDADG (SEQ ID NO: 55) meganuclease selected from I-DmoI, I-SceI and I-AniI.

Wild-type mono-LAGLIDADG (SEQ ID NO: 55) meganucleases include, without limitation, the I-CreI meganuclease of SEQ ID NO: 1, the I-MsoI meganuclease of SEQ ID NO: 2, and the I-CeuI meganuclease of SEQ ID NO: 3. Wild-type di-LAGLIDADG (SEQ ID NO: 55) meganucleases include, without limitation, the I-DmoI meganuclease of SEQ ID NO: 4, the I-SceI meganuclease of SEQ ID NO: 5, and the 1-AniI meganuclease of SEQ ID NO: 6.

Wild-type LAGLIDADG (SEQ ID NO: 55) domains include, without limitation, residues 9-151 of the wild-type I-CreI meganuclease of SEQ ID NO: 1; residues 11-162 of the wild-type I-MsoI meganuclease of SEQ ID NO: 2; and residues 55-210 of the wild-type I-CeuI meganuclease of SEQ ID NO: 3, residues 9-96 of the wild-type I-DmoI of SEQ ID NO: 4; residues 105-178 of the wild-type I-DmoI of SEQ ID NO: 4; residues 32-123 of the wild-type 1-SceI of SEQ ID NO: 5; residues 134-225 of the wild-type I-SceI of SEQ ID NO: 5; residues 4-121 of the wild-type I-AniI of SEQ ID NO: 6; and residues 136-254 of the wild-type I-AniI of SEQ ID NO: 6.

LAGLIDADG (SEQ ID NO: 55) subunits derived from a wild-type LAGLIDADG (SEQ ID NO: 55) meganuclease include, without limitation, subunits including a LAGLIDADG (SEQ ID NO: 55) domain that has at least 85% sequence identity, or 85%100% sequence identity, to any one of residues 9-151 of the wild-type I-CreI meganuclease of SEQ ID NO: 1; residues 11-162 of the wild-type I-MsoI meganuclease of SEQ ID NO: 2; and residues 55-210 of the wild-type I-CeuI meganuclease of SEQ ID NO: 3, residues 9-96 of the wild-type I-DmoI of SEQ ID NO: 4; residues 105-178 of the wild-type I-DmoI of SEQ ID NO: 4; residues 32-123 of the wild-type I-SceI of SEQ ID NO: 5; residues 134-225 of the wild-type I-SceI of SEQ ID NO: 5; residues 4-121 of the wild-type I-AniI of SEQ ID NO: 6; and residues 136-254 of the wild-type I-AniI of SEQ ID NO: 6.

LAGLIDADG (SEQ ID NO: 55) subunits derived from a wild-type LAGLIDADG (SEQ ID NO: 55) meganuclease also include, without limitation, subunits comprising any of the foregoing polypeptide sequences in which one or more amino acid modifications have been included according to the methods of rationally-designing LAGLIDADG (SEQ ID NO: 55) meganucleases disclosed in WO 2007/047859, as well as other non-naturally-occurring meganuclease variants known in the art.

In certain embodiments, the invention provides recombinant single-chain meganucleases comprising a pair of LAGLIDADG (SEQ ID NO: 55) subunits derived from naturally-occurring LAGLIDADG (SEQ ID NO: 55) subunits each of which recognizes a wild-type DNA half-site selected from SEQ ID NOs: 7-30.

In other embodiments, the invention provides recombinant single-chain meganucleases comprising a pair of LAGLIDADG (SEQ ID NO: 55) subunits genetically engineered with respect to DNA-binding specificity, each of which recognizes a DNA half-site that differs by at least one base from a wild-type DNA half-site selected from SEQ ID NOs: 7-30.

In other embodiments, the invention provides recombinant single-chain meganucleases comprising a pair of LAGLIDADG (SEQ ID NO: 55) subunits in which one subunit is natural and recognizes a wild-type DNA half-site selected SEQ ID NOs: 7-30 and the other is genetically engineered with respect to DNA-binding specificity and recognizes a DNA site that differs by at least one base from a wild-type DNA half-site selected from SEQ ID NOs: 7-30.

In some embodiments, the polypeptide linker joining the LAGLIDADG (SEQ ID NO: 55) subunits is a flexible linker. In particular embodiments, the linker can include 15-40 residues, 25-31 residues, or any number within those ranges. In other particular embodiments, at least 50%, or 50%-100%, of the residues forming the linker are polar uncharged residues.

In other embodiments, the polypeptide linker joining the LAGLIDADG (SEQ ID NO: 55) subunits has a stable secondary structure. In particular embodiments, the stable secondary structure comprises at least two α-helix structures in other particular embodiments, the stable secondary structure comprises from N-terminus to C-terminus a first loop, a first α-helix, a first turn, a second α-helix, and a second loop. In some particular embodiments, the linker can include 23-56 residues, or any number within that range.

In some embodiments, the polypeptide linker joining the LAGLIDADG subunits is a flexible linker. In particular embodiments, the linker can include 15-40 residues, 25-31 residues, or any number within those ranges. In other particular embodiments, at least 50%, or 50%-100%, of the residues forming the linker are polar uncharged residues.

In other embodiments, the polypeptide linker joining the LAGLIDADG subunits has a stable secondary structure. In particular embodiments, the stable secondary structure comprises at least two α-helix structures. In other particular embodiments, the stable secondary structure comprises from N-terminus to C-terminus a first loop, a first α-helix, a first turn, a second α-helix, and a second loop. In some particular embodiments, the linker can include 23-56 residues, or any number within that range.

In another aspect, the invention provides for various methods of use for the single-chain meganucleases described and enabled herein. These methods include producing genetically-modified cells and organisms, treating diseases by gene therapy, treating pathogen infections, and using the recombinant single-chain meganucleases for in vitro applications for diagnostics and research.

Thus, in one aspect, the invention provides methods for producing a genetically-modified eukaryotic cell including an exogenous sequence of interest inserted in a chromosome, by transfecting the cell with (i) a first nucleic acid sequence encoding a meganuclease of the invention, and (ii) a second nucleic acid sequence including said sequence of interest, wherein the meganuclease produces a cleavage site in the chromosome and the sequence of interest is inserted into the chromosome at the cleavage site either by homologous recombination or non-homologous end-joining.

Alternatively, in another aspect, the invention provides methods for producing a genetically-modified eukaryotic cell including an exogenous sequence of interest inserted in a chromosome, by introducing a meganuclease protein of the invention into the cell, and transfecting the cell with a nucleic acid including the sequence of interest, wherein the meganuclease produces a cleavage site in the chromosome and the sequence of interest is inserted into the chromosome at the cleavage site either by homologous recombination or non-homologous end joining.

In another aspect, the invention provides methods for producing a genetically-modified eukaryotic cell by disrupting a target sequence in a chromosome, by transfecting the cell with a nucleic acid encoding a meganuclease of the invention, wherein the meganuclease produces a cleavage site in the chromosome and the target sequence is disrupted by non-homologous end joining at the cleavage site.

In another aspect, the invention provides methods of producing a genetically-modified organism by producing a genetically-modified eukaryotic cell according to the methods described above, and growing the genetically-modified eukaryotic cell to produce the genetically-modified organism. In these embodiments, the eukaryotic cell can be selected from a gamete, a zygote, a blastocyst cell, an embryonic stem cell, and a protoplast cell.

In another aspect, the invention provides methods for treating a disease by gene therapy in a eukaryote, by transfecting at least one cell of the eukaryote with one or more nucleic acids including (i) a first nucleic acid sequence encoding a meganuclease of the invention, and (ii) a second nucleic acid sequence including a sequence of interest, wherein the meganuclease produces a cleavage site in the chromosome and the sequence of interest is inserted into the chromosome by homologous recombination or non-homologous end-joining, and insertion of the sequence of interest provides gene therapy for the disease.

Alternatively, in another aspect, the invention provides methods for treating a disease by gene therapy in a eukaryote, by introducing a meganuclease protein of the invention into at least one cell of the eukaryote, and transfecting the cell with a nucleic acid including a sequence of interest, wherein the meganuclease produces a cleavage site in the chromosome and the sequence of interest is inserted into the chromosome at the cleavage site by homologous recombination or non-homologous end-joining, and insertion of the sequence of interest provides gene therapy for the disease.

In another aspect, the invention provides methods for treating a disease by gene therapy in a eukaryote by disrupting a target sequence in a chromosome of the eukaryotic, by transfecting at least one cell of the eukaryote with a nucleic acid encoding a meganuclease of the invention, wherein the meganuclease produces a cleavage site in the chromosome and the target sequence is disrupted by non-homologous end joining at the cleavage site, wherein disruption of the target sequence provides the gene therapy for the disease.

In another aspect, the invention provides methods for treating a viral or prokaryotic pathogen infection in a eukaryotic host by disrupting a target sequence in a genome of the pathogen, by transfecting at least one infected cell of the host with a nucleic acid encoding a meganuclease of the invention, wherein the meganuclease produces a cleavage site in the genome and the target sequence is disrupted by either (1) non-homologous end joining at the cleavage site or (2) by homologous recombination with a second nucleic acid, and wherein disruption of the target sequence provides treatment for the infection.

These and other aspects and embodiments of the invention will be apparent to one of ordinary skill in the art based upon the following detailed description of the invention.

BRIEF DESCRIPTION OF THE DRAWING

FIG. 1 is a diagram of the structural components of one embodiment of a linker of the invention (Linker 9) and N-terminal and C-terminal residues of the endonuclease subunits joined by the linker (SEQ ID NO: 109).

DETAILED DESCRIPTION OF THE INVENTION 1.1 Introduction

The present invention is based, in part, upon the development of fusion proteins in which a peptide linker covalently joins two heterologous LAGLIDADG (SEQ ID NO: 55) meganuclease subunits to form a "single-chain heterodimer meganuclease" in which the subunits function together to preferentially bind to and cleave a non-palindromic DNA recognition site which is a hybrid of the recognition half-sites of the two subunits. In particular, the invention can be used to genetically engineer single-chain meganucleases which recognize non-palindromic DNA sequences that naturally-occurring meganucleases do not recognize.

This discovery has been used, as is described in detail below, to join mono-LAGLIDADG (SEQ ID NO: 55) meganucleases, which naturally function as homodimers, into single-chain meganucleases. Further, the discovery has been used to join mono-LAGLIDADG (SEQ ID NO: 55) meganucleases which have been re-engineered with respect to DNA-recognition specificity into single-chain heterodimers which recognize and cleave DNA sequences that are a hybrid of the palindromic sites recognized by the two meganuclease homodimers. The invention provides exemplary peptide linker sequences for joining LAGLIDADG (SEQ ID NO: 55) subunits into single polypeptides. Importantly, the invention provides a general method for the production of linker sequences and the selection of fusion points for linking different LAGLIDADG (SEQ ID NO: 55) subunits to produce functional rationally-designed single-chain meganucleases.

The invention also provides methods that use such meganucleases to produce recombinant nucleic acids, cells and organisms by utilizing the meganucleases to cause recombination of a desired genetic sequence at a limited number of loci within the genome of the organism for, inter alia, genetic engineering, gene therapy, treatment of pathogenic infections and cancer, and in vitro applications in diagnostics and research.

As a general matter, the invention provides methods for generating single-chain meganucleases comprising two LAGLIDADG (SEQ ID NO: 55) subunits in which the N-terminal subunit is derived from a natural mono-LAGLIDADG (SEQ ID NO: 55) meganuclease such as I-CreI, I-MsoI, or I-CeuI or a variant thereof and the C-terminal subunit is derived from either a mono-LAGLIDADG (SEQ ID NO: 55) meganuclease or one of the two domains of a di-LAGLIDADG (SEQ ID NO: 55) meganuclease such as I-SceI, I-DmoI, or I-AniI. The method is distinct from those described previously (Epinat et al. (2003), *Nucleic Acids Res.* 31: 2952-62; Chevalier et al. (2002), *Mol. Cell.* 10:895-905; WO 2003/078619) in that it requires the use of specific and novel linker sequences and fusion points to produce recombinant single-chain meganucleases in which the N-terminal subunit is derived from a mono-LAGLIDADG (SEQ ID NO: 55) meganuclease.

As described in detail below, the method of producing a recombinant single-chain meganuclease includes the use of defined fusion points in the two LAGLIDADG (SEQ ID NO: 55) subunits to be joined as well as the use of defined linker sequences to join them into a single polypeptide. In addition, a set of rules is provided for identifying fusion points not explicitly described herein as well as for producing functional linker sequences that are not explicitly described herein.

Thus, in one aspect, the invention provides methods for producing recombinant single-chain LAGLIDADG (SEQ ID NO: 55) meganucleases. In another aspect, the invention provides the recombinant single-chain meganucleases resulting from these methods. In another aspect, the invention provides methods that use such single-chain meganucleases to produce recombinant nucleic acids, cells and organisms in which a desired DNA sequence or genetic locus within the genome of cell or organism is modified by the insertion, deletion, substitution or other manipulation of DNA sequences. In another aspect, the invention provides methods for reducing the survival of pathogens or cancer cells using single-chain meganucleases which have pathogen-specific or cancer-specific recognition sequences.

1.2 References and Definitions

The patent and scientific literature referred to herein establishes knowledge that is available to those of skill in the art. The issued U.S. patents, allowed applications, published U.S. and PCT international applications, and references, including GenBank database sequences, that are cited herein are hereby incorporated by reference to the same extent as if each was specifically and individually indicated to be incorporated by reference.

As used herein, the term "meganuclease" refers to an endonuclease that binds double-stranded DNA at a recognition sequence that is greater than 12 base pairs in length. Naturally-occurring meganucleases can be monomeric (e.g., I-SceI) or dimeric (e.g., I-CreI). The term meganuclease, as used herein, can be used to refer to monomeric meganucleases, dimeric meganucleases, to the monomers which associate to form a dimeric meganuclease, or to a recombinant single-chain meganuclease of the invention. The term "homing endonuclease" is synonymous with the term "meganuclease."

As used herein, the term "LAGLIDADG (SEQ ID NO: 55) meganuclease" refers either to meganucleases including a single LAGLIDADG (SEQ ID NO: 55) motif, which are naturally dimeric, or to meganucleases including two LAGLIDADG (SEQ ID NO: 55) motifs, which are naturally monomeric. The term "mono-LAGLIDADG (SEQ ID NO: 55) meganuclease" is used herein to refer to meganucleases including a single LAGLIDADG (SEQ ID NO: 55) motif, and the term "di-LAGLIDADG (SEQ ID NO: 55) meganuclease" is used herein to refer to meganucleases including two LAGLIDADG (SEQ ID NO: 55) motifs, when it is necessary to distinguish between the two. Each of the two structural domains of a di-LAGLIDADG (SEQ ID NO: 55) meganuclease which includes a LAGLIDADG (SEQ ID NO: 55) motif and has enzymatic activity, and each of the individual monomers of a mono-LAGLIDADG (SEQ ID NO: 55) meganuclease, can be referred to as a LAGLIDADG (SEQ ID NO: 55) subunit, or simply "subunit".

As used herein, and in reference to a peptide sequence, "end" refers to the C-terminus and "beginning" refers to the N-terminus. Thus, for example, "the beginning of the LAGLIDADG (SEQ ID NO: 55) motif" refers to the N-terminal-most amino acid in the peptide sequence comprising the LAGLIDADG (SEQ ID NO: 55) motif whereas "the end of the LAGLIDADG (SEQ ID NO: 55) motif" refers to the C-terminal-most amino acid in the peptide sequence comprising the LAGLIDADG (SEQ ID NO: 55) motif.

As used herein, the term "rationally-designed" means non-naturally-occurring and/or genetically engineered. The rationally-designed meganucleases of the invention differ from wild-type or naturally-occurring meganucleases in their amino acid sequence or primary structure, and may also differ in their secondary, tertiary or quaternary structure. In addition, the rationally-designed meganucleases of the invention also differ from wild-type or naturally-occurring meganucleases in recognition sequence-specificity and/or activity.

As used herein, with respect to a protein, the term "recombinant" means having an altered amino acid sequence as a result of the application of genetic engineering techniques to nucleic acids which encode the protein, and cells or organisms which express the protein. With respect to a nucleic acid, the term "recombinant" means having an altered nucleic acid sequence as a result of the application of genetic engineering techniques. Genetic engineering techniques include, but are not limited to, PCR and DNA cloning technologies; transfection, transformation and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant.

As used herein with respect to recombinant proteins, the term "modification" means any insertion, deletion or substitution of an amino acid residue in the recombinant sequence relative to a reference sequence (e.g., a wild-type).

As used herein, the term "genetically-modified" refers to a cell or organism in which, or in an ancestor of which, a genomic DNA sequence has been deliberately modified by recombinant technology. As used herein, the term "genetically-modified" encompasses the term "transgenic."

As used herein, the term "wild-type" refers to any naturally-occurring form of a meganuclease. The term "wild-type" is not intended to mean the most common allelic variant of the enzyme in nature but, rather, any allelic variant found in nature. Wild-type meganucleases are distinguished from recombinant or non-naturally-occurring meganucleases.

As used herein, the term "recognition sequence half-site" or simply "half site" means a nucleic acid sequence in a double-stranded DNA molecule which is recognized by a monomer of a mono-LAGLIDADG (SEQ ID NO: 55) meganuclease or by one LAGLIDADG (SEQ ID NO: 55) subunit, of a di-LAGLIDADG meganuclease.

As used herein, the term "recognition sequence" refers to a pair of half-sites which is bound and cleaved by either a mono-LAGLIDADG (SEQ ID NO: 55) meganuclease dimer or a di-LAGLIDADG (SEQ ID NO: 55) meganuclease monomer. The two half-sites may or may not be separated by base pairs that are not specifically recognized by the enzyme. In the cases of I-CreI, I-MsoI and I-CeuI, the recognition sequence half-site of each monomer spans 9 base pairs, and the two half-sites are separated by four base pairs which are not contacted directly by binding of the enzyme but which constitute the actual cleavage site (which has a 4 base pair overhang). Thus, the combined recognition sequences of the I-CreI, I-MsoI and I-CeuI meganuclease dimers normally span 22 base pairs, including two 9 base pair half-sites flanking a 4 base pair cleavage site. In the case of the I-SceI meganuclease, which is a di-LAGLIDADG (SEQ ID NO: 55) meganuclease monomer, the recognition sequence is an approximately 18 bp non-palindromic sequence, and there are no central base pairs which are not specifically recognized. By convention, one of the two strands is referred to as the "sense" strand and the other the "antisense" strand, although neither strand may encode protein.

As used herein, the term "specificity" means the ability of a meganuclease to recognize and cleave double-stranded DNA molecules only at a particular sequence of base pairs referred to as the recognition sequence, or only at a particular set of recognition sequences. The set of recognition sequences will share certain conserved positions or sequence motifs, but may be degenerate at one or more positions. A highly-specific meganuclease is capable of cleaving only one or a very few recognition sequences. Specificity can be determined in a cleavage assay as described in Example 1. As used herein, a meganuclease has "altered" specificity if it binds to and cleaves a recognition sequence which is not bound to and cleaved by a reference meganuclease (e.g., a wild-type) under physiological conditions, or if the rate of cleavage of a recognition sequence is increased or decreased by a biologically significant amount (e.g., at least 2×, or 2×-10×) relative to a reference meganuclease.

As used herein, the term "palindromic" refers to a recognition sequence consisting of inverted repeats of identical half-sites. However, the palindromic sequence need not be palindromic with respect to the central base pairs which are not directly contacted by binding of the enzyme (e.g., the four central base pairs of an I-CreI recognition site). In the case of naturally-occurring dimeric meganucleases, palindromic DNA sequences are recognized by homodimers in which the two monomers make contacts with identical half-sites.

As used herein, the term "pseudo-palindromic" refers to a recognition sequence consisting of inverted repeats of non-identical or imperfectly palindromic half-sites. In addition to central base pairs that are not directly contacted by binding of the enzyme, the pseudo-palindromic sequence can deviate from a palindromic sequence between the two recognition half-sites at 1-3 base pairs at each of the two half-sites. Pseudo-palindromic DNA sequences are typical of the natural DNA sites recognized by wild-type homodimeric meganucleases in which two identical enzyme monomers make contacts with slightly different half-sites.

As used herein, the term "non-palindromic" refers to a recognition sequence composed of two unrelated half-sites of a meganuclease. In this case, the non-palindromic sequence need not be palindromic with respect to either the central base pairs or 4 or more base pairs at each of the two half-sites. Non-palindromic DNA sequences are recognized by either di-LAGLIDADG (SEQ ID NO: 55) meganucleases, highly degenerate mono-LAGLIDADG (SEQ ID NO 55) meganucleases (e.g., I-CeuI) or by heterodimers of mono-LAGLIDADG (SEQ ID NO: 55) meganuclease monomers that recognize non-identical half-sites. In the latter case, a non-palindromic recognition sequence may be referred to as a "hybrid sequence" because the heterodimer of two different mono-LAGLIDADG (SEQ ID NO: 55) monomers, whether or not they are fused into a single polypeptide, will cleave a recognition sequence comprising one half-site recognized by each monomer. Thus, the heterodimer recognition sequence is a hybrid of the two homodimer recognition sequences.

As used herein, the term "linker" refers to an exogenous peptide sequence used to join two LAGLIDADG (SEQ ID NO: 55) subunits into a single polypeptide. A linker may have a sequence that is found in natural proteins, or may be an artificial sequence that is not found in any natural protein. A linker may be flexible and lacking in secondary structure or may have a propensity to form a specific three-dimensional structure under physiological conditions.

As used herein, the term "fusion point" refers to the junction between a LAGLIDADG (SEQ ID NO: 55) subunit and a linker. Specifically, the "N-terminal fusion point" is the last (C-terminal-most) amino acid of the N-terminal LAGLIDADG (SEQ ID NO: 55) subunit prior to the linker sequence and the "C-terminal fusion point" is the first (N-terminal-most) amino acid of the C-terminal LAGLIDADG (SEQ ID NO: 55) subunit following the linker sequence.

As used herein, the term "single-chain meganuclease" refers to a polypeptide comprising a pair of LAGLIDADG (SEQ ID NO: 55) subunits joined by a linker. A single-chain meganuclease has the organization: N-terminal subunit—Linker—C-terminal subunit. A single-chain meganuclease is distinguished from a natural di-LAGLIDADG (SEQ ID NO: 55) meganuclease in that the N-terminal subunit must be derived from a mono-LAGLIDADG (SEQ ID NO: 55) meganuclease and, therefore, the linker must be exogenous to the N-terminal subunit.

As used herein, the term "homologous recombination" refers to the natural, cellular process in which a double-stranded DNA-break is repaired using a homologous DNA sequence as the repair template (see, e.g., Cahill et al. (2006), *Front. Biosci.* 11:1958-1976). The homologous DNA sequence may be an endogenous chromosomal sequence or an exogenous nucleic acid that was delivered to the cell. Thus, in some embodiments, a rationally-designed meganuclease is used to cleave a recognition sequence within a target sequence and an exogenous nucleic acid with homology to or substantial sequence similarity with the target sequence is delivered into the cell and used as a template for repair by homologous recombination. The DNA sequence of the exogenous nucleic acid, which may differ significantly from the target sequence, is thereby incorporated into the chromosomal sequence. The process of homologous recombination occurs primarily in eukaryotic organisms. The term "homology" is used herein as equivalent to "sequence similarity" and is not intended to require identity by descent or phylogenetic relatedness.

As used herein, the term "non-homologous end-joining" refers to the natural, cellular process in which a double-stranded DNA-break is repaired by the direct joining of two non-homologous DNA segments (see, e.g. Cahill et al. (2006), *Front. Biosci.* 11:1958-1976). DNA repair by non-homologous end joining is error-prone and frequently results in the untemplated addition or deletion of DNA sequences at the site of repair. Thus, in certain embodiments, a rationally-designed meganuclease can be used to produce a double-stranded break at a meganuclease recognition sequence within a target sequence to disrupt a gene (e.g., by introducing base insertions, base deletions, or frame-shift mutations) by non-homologous end-joining. In other embodiments, an exogenous nucleic acid lacking homology to or substantial sequence similarity with the target sequence may be captured at the site of a meganuclease-stimulated double-stranded DNA break by non-homologous end joining (see, e.g., Salomon et al. (1998), *EMBO J.* 17:6086-6095). The process of non-homologous end joining occurs in both eukaryotes and prokaryotes such as bacteria.

As used herein, the term "sequence of interest" means any nucleic acid sequence, whether it codes for a protein, RNA, or regulatory element (e.g., an enhancer, silencer, or promoter sequence), that can be inserted into a genome or used to replace a genomic DNA sequence using a meganuclease protein. Sequences of interest can have heterologous DNA sequences that allow for tagging a protein or RNA that is expressed from the sequence of interest. For instance, a protein can be tagged with tags including, but not limited to, an epitope (e.g., c-myc, FLAG) or other ligand (e.g., poly-His). Furthermore, a sequence of interest can encode a fusion protein, according to techniques known in the art (see, e.g., Ausubel et al., *Current Protocols in Molecular Biology*, Wiley 1999). In some embodiments, the sequence of interest is flanked by a DNA sequence that is recognized by the recombinant meganuclease for cleavage. Thus, the flanking sequences are cleaved allowing for proper insertion of the sequence of interest into genomic recognition sequences cleaved by the recombinant meganuclease. In some embodiments, the entire sequence of interest is homologous to or has substantial sequence similarity with a target sequence in the genome such that homologous recombination effectively replaces the target sequence with the sequence of interest. In other embodiments, the sequence of interest is flanked by DNA sequences with homology to or substantial sequence similarity with the target sequence such that homologous recombination inserts the sequence of interest within the genome at the locus of the target sequence. In some embodiments, the sequence of interest is substantially identical to the target sequence except for mutations or other modifications in the meganuclease recognition sequence such that the meganuclease can not cleave the target sequence after it has been modified by the sequence of interest.

As used herein with respect to both amino acid sequences and nucleic acid sequences, the terms "percentage similarity" and "sequence similarity" refer to a measure of the degree of similarity of two sequences based upon an alignment of the sequences which maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (www.ncbi.nlm.nih.gov/), and are described in, for example, Altschul et al. (1990), *J. Mol. Biol.* 215:403-410; Gish and States (1993), *Nature Genet.* 3:266-272; Madden et al. (1996), *Meth. Enzymol.* 266:131-141; Altschul et al. (1997), *Nucleic Acids Res.* 25:33 89-3402); Zhang et al. (2000), *J. Comput. Biol.* 7(1-2):203-14. As used herein, percent similarity of two amino acid sequences is the score based upon the following parameters for the BLASTp algorithm: word size=3; gap opening penalty=-11; gap extension penalty=-1; and scoring matrix=BLOSUM62. As used herein, percent similarity of two nucleic acid sequences is the score based upon the following parameters for the BLASTn algorithm: word size=11; gap opening penalty=-5; gap extension penalty=-2; match reward=1; and mismatch penalty=-3.

As used herein with respect to modifications of two proteins or amino acid sequences, the term "corresponding to" is used to indicate that a specified modification in the first protein is a substitution of the same amino acid residue as in the modification in the second protein, and that the amino acid position of the modification in the first proteins corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment, and despite the fact that X and Y may be different numbers.

As used herein, the recitation of a numerical range for a variable is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values $\geq 0$ and $\leq 2$ if the variable is inherently continuous.

As used herein, unless specifically indicated otherwise, the word "or" is used in the inclusive sense of "and/or" and not the exclusive sense of "either/or."

2. Single-Chain Meganucleases Derived from LAGLIDADG (SEQ ID NO: 55) Subunits

Structural comparisons of natural mono- and di-LAGLIDADG (SEQ ID NO: 55) meganucleases reveal that the N-terminal subunits of di-LAGLIDADG (SEQ ID NO: 55) meganucleases tend to be smaller than mono-LAGLIDADG (SEQ ID NO: 55) monomers. The consequence of this is that, in the case of di-LAGLIDADG (SEQ ID NO: 55) meganucleases, the end (C-terminus) of the N-terminal subunit is much closer to the start (N-terminus) of the C-terminal subunit. This means that a relatively short (e.g., 5-20 amino acid) linker is sufficient to join the two subunits. In the case of mono-LAGLIDADG (SEQ ID NO 55) meganucleases, the C-terminus of one monomer is generally very far (approximately 48 Å in the case of I-CreI) from the N-terminus of the second monomer. Therefore, fusing a pair of mono-LAGLIDADG (SEQ ID NO: 55) meganucleases into a single polypeptide requires a longer (e.g., >20 amino acid) peptide linker which can span this distance. An alternative method, in which the N-terminal subunit is truncated at a point spatially closer to the start of the C-terminal subunit has been reported previously (Epinat et al. (2003), *Nucleic Acids Res.* 31: 2952-62; WO 2003/078619), but produces little if any functional heterodimer, as shown in Example 1 below. An extensive discussion regarding the difficulty associated with producing a functional single-chain meganuclease derived from I-CreI can be found in Fajardo-Sanchez et al. (2008), *Nucleic Acids Res.* 36:2163-2173.

2.1 Fusion Points for ICreI

A series of truncation mutants were made in which either wild-type I-CreI or an engineered variant of I-CreI which had been altered with respect to its DNA cleavage site preference (designated "CCR2", SEQ ID NO: 31; see WO 2007/047859) were terminated prior to the natural C-terminal amino acid, Pro 163 (Table 1). The mutant homodimers were expressed in *E. coli*, purified, and incubated with either the wild-type recognition sequence (SEQ ID NOs: 34-35) or the CCR2 recognition sequence (SEQ ID NOs: 32-33) to test for cleavage activity.

TABLE 1

| I-CreI Truncation Mutants | | |
| --- | --- | --- |
| C-terminal amino acid | Wild-type activity | CCR2 activity |
| Asp-153 | + | + |
| Val-151 | + | + |
| Val-148 | + | − |
| Arg-141 | − | − |
| Asn-136 | − | − |
| Val-129 | − | − |
| Ile-109 | − | − |
| Leu-95 | − | − |

Wild-type I-CreI was found to be active when truncated at residue 148 or further C-terminal residues, but inactive when truncated at residue 141 or further N-terminal residues. Therefore, at least some of residues 141 through 147, or conservative substitutions of those residues, are required for wild-type activity. Similarly, CCR2 was found to be active when truncated at residue 151 or further C-terminal residues, but inactive when terminated at residue 148 or further N-terminal residues. Therefore, at least some of residues 148 through 150, or conservative substitutions of those residues, are required for CCR2 activity. The difference between the wild-type I-CreI and the rationally-designed CCR2 meganuclease is presumably due to a reduction in the structural stability of the CCR2 meganuclease such that it is more sensitive to further destabilization by a premature C-terminal truncation. These truncation results are consistent with a publication from Prieto et al. in which it was found that the C-terminal loop of I-CreI (amino acids 138-142) is essential for cleavage activity (Prieto et al. (2007), *Nucl. Acids Res.* 35:3262-3271). Taken together, these results indicate that some residues near the C-terminus of I-CreI are essential for DNA-binding and/or catalytic activity and methods for single-chain meganuclease production that truncate an I-CreI subunit prior to approximately residue 142 (e.g., Epinat et al. (2003), *Nucl. Acids Res.* 31: 2952-62; WO 2003/078619) are unlikely to yield a single-chain meganuclease in which both LAGLIDADG (SEQ ID NO: 55) subunits are catalytically active.

Therefore, in accordance with the present invention, the N-terminal fusion point (i.e., between the N-terminal I-CreI subunit and the linker) should lie at or C-terminal to residue 142 of the N-terminal subunit, including any of positions 142-151, or any position C-terminal to residue 151. Residues 154-163 of I-CreI are unstructured (Jurica et al. (1998), *Mol. Cell.* 2:469-476) and, therefore, inclusion of these residues will increase the flexibility and, possibly, structural instability of the resultant single-chain meganuclease. Conversely, if it is determined that less flexibility and greater structural stability are desired or required, fusion points at residues 142-153 can be chosen.

When the C-terminal LAGLIDADG (SEQ ID NO: 55) subunit of a single-chain meganuclease is derived from I-CreI, the C-terminal fusion point of the linker will be toward the N-terminus of the I-CreI sequence. Residues 7, 8 and 9 are of particular interest as C-terminal fusion points in I-CreI because these residues (1) are structurally conserved among LAGLIDADG (SEQ ID NO: 55) meganuclease family members and, therefore, may provide greater compatibility in forming heterodimers with other LAGLIDADG(SEQ ID NO: 55) family members, and (2) initiate an alpha-helix containing the conserved LAGLIDADG (SEQ ID NO: 55) motif that is involved in catalytic function. However, fusion points N-terminal to residue 7, including any of residues 1-6, can also be employed in accordance with the invention.

The following I-CreI N-terminal and C-terminal fusion points were chosen for further experimentation, but should not be regarded as limiting the scope of the invention:

TABLE 2

I-CreI Fusion Points

| N-terminal fusion point | C-terminal fusion point |
| --- | --- |
| Val-151 | Lys-7 |
| Leu-152 | Asp-8 |
| Asp-153 | Phe-9 |

2.2 Linkers for Single-Chain Meganucleases Derived from I-CreI

For the purpose of linking a pair of I-CreI monomers into a single polypeptide, two general classes of linker were considered: (1) an unstructured linker lacking secondary structure; and (2) a structured linker having secondary structure. Examples of unstructured linkers are well known in the art, and include artificial sequences with high Gly and Ser content, or repeats. Structured linkers are also well known in the art, and include those designed using basic principles of protein folding (e.g., Aurora and Rose (1998), *Protein Sci.* 7:21-38; Fersht, *Structure and Mechanism in Protein Science*, W.H. Freeman 1998).

The invention was validated using a pair of rationally-designed I-CreI monomers called "LAM1" (SEQ ID NO: 36) and "LAM2" (SEQ ID NO: 37). These rationally-designed endonucleases were produced using the methods described in WO 2007/047859 and they are characterized therein. As will be apparent to those of skill in the art, however, the LAM1 and LAM2 monomers are merely exemplary of the many monomers which can be employed, including wild-type mono-LAGLIDADG (SEQ ID NO: 55) subunits, N-terminally and/or C-terminally truncated wild-type mono-LAGLIDADG (SEQ ID NO: 55) subunits, N-terminally and/or C-terminally truncated wild-type di-LAGLIDADG (SEQ ID NO: 55) subunits, and rationally designed modifications of any of the foregoing.

One exemplary monomer, LAM1, differs by 7 amino acids from wild-type I-CreI and recognizes the half site:

```
5'-TGCGGTGTC-3'        (SEQ ID NO: 38)
3'-ACGCCACAG-5'        (SEQ ID NO: 39)
```

Thus, the LAM1 homodimer recognizes the palindromic recognition sequence (where each N is unconstrained):

```
5'-TGCGGTGTCNNNNGACACCGCA-3'     (SEQ ID NO: 40)
3'-ACGCCACAGNNNNCTGTGGCGT-5'     (SEQ ID NO: 41)
```

The other exemplary monomer, LAM2, differs by 5 amino acids from wild-type I-CreI and recognizes the half-site:

```
5'-CAGGCTGTC-3'        (SEQ ID NO: 42)
3'-GTCCGACAG-5'        (SEQ ID NO: 43)
```

Thus, the LAM2 homodimer recognizes the palindromic recognition sequence (where each N is unconstrained):

```
5'-CAGGCTGTCNNNNGACAGCCTG-3'     (SEQ ID NO: 44)
3'-GTCCGACAGNNNNCTGTCGGAC-5'     (SEQ ID NO: 45)
```

A heterodimer comprising one LAM1 monomer and one LAM2 monomer ("LAM1/LAM2 heterodimer") thus recognizes the hybrid recognition sequence:

```
5'-TGCGGTGTCNNNNGACAGCCTG-3'     (SEQ ID NO: 56)
3'-ACGCCACAGNNNNCTGTCGGAC-5'     (SEQ ID NO: 57)
```

2.2.1 Flexible Linkers for Single-Chain Meganucleases

A variety of highly-flexible peptide linkers are known in the art and can be used in accordance with the invention. For example, and without limitation, peptide linkers comprising repeating Gly-Ser-Ser units are known to be unstructured and flexible (Fersht, *Structure and Mechanism in Protein Science*, W.H. Freeman 1998). Linkers with this and similar compositions are frequently used to fuse protein domains together (e.g., single-chain antibodies (Mack et al. (1995), *Proc. Nat. Acad. Sci.* 92:7021-7025); growth factor receptors (Ueda et al. (2000), *J. Immunol. Methods* 241:159-170); enzymes (Brodelius et al. (2002), 269:3570-3577); and DNA-binding and nuclease domains (Kim et al. (1996), *Proc. Nat. Acad. Sci.* 93:1156-1160).

As a general matter, the flexible linker can include any polypeptide sequence which does not form stable secondary structures under physiological conditions. In some embodiments, the linkers include a high percentage (e.g., >50%, 60%, 70%, 80% or 90%, or generally, 50%-100%) of polar uncharged residues (i.e., Gly, Ser, Cys, Asn, Gln, Tyr, Thr). In addition, in some embodiments, the linkers include a low percentage of large hydrophobic residues (i.e., Phe, Trp, Met). The linkers may include repeats of varying lengths (e.g., $(SG)_n$, $(GSS)_n$, $(SGGS)_n$, (SEQ ID NO: 58)), may include random sequences, or may include combinations of the two.

Thus, in accordance with the invention, a set of single-chain fusions between LAM1 and LAM2 were produced in which a highly-flexible peptide linker covalently joined the N-terminal (LAM1) subunit to the C-terminal (LAM2) subunit using Val-151 or Asp-153 as the N-terminal fusion point and Phe-9 as the C-terminal fusion point. The single-chain proteins were expressed in *E. coli*, purified, and tested for the ability to cleave a hybrid DNA site comprising one LAM1 half-site and one LAM2 half-site (SEQ ID NOs: 46 and 47). Cleavage activity was rated on a four point scale: − no detectable activity; + minimal activity; ++ medium activity; +++ activity comparable to the LAM1/LAM2 heterodimer produced by co-expression of the two monomers in *E. coli* prior to endonuclease purification. The proteins were also evaluated by SDS-PAGE to determine the extent to which the linker region was proteolyzed during expression or purification to release the two subunits.

kilodaltons). Numbers 3 and 8 have the same linker sequence but N-terminal fusion points at Val-151 and Asp-153, respectively. Both single-chain meganucleases exhibited comparable levels of activity, indicating that the precise fusion point is not critical in this instance. Finally, linkers 4 and 5, comprising 31 and 34 amino acids, respectively, yielded no detectable single-chain meganuclease when purified from *E. coli*. These linkers were completely proteolyzed to the individual LAM1 and/or LAM2 subunits as detected by SDS-PAGE and, therefore, the cleavage activity of these meganucleases was not investigated further.

These results led us to conclude that Gly-Ser linkers are acceptable for the production of single-chain meganucleases based upon the LAGLIDADG (SEQ ID NO: 55) subunit of the mono-LAGLIDADG (SEQ ID NO: 55) meganuclease I-CreI and the particular fusion points employed, provided that the linkers are greater than 25 and less than 31 amino acids in length. For I-CreI-based single-chain meganucleases with these fusion points, shorter linkers prevent catalysis while longer linkers are unstable and prone to clipping by proteases.

The effects of varying the fusions points on the acceptable linker lengths can be determined empirically by routine experimentation and/or predicted based upon three-dimensional modeling of the protein structures. Significantly, as a fusion point is moved either N-terminally or C-terminally, it may move either closer or farther from the other fusion point depending upon the secondary and tertiary structure of the protein near the fusion point. Thus, for example, moving the N-terminal fusion point in the C-terminal direction (e.g., from residue 150 to residue 155 for an N-terminal subunit) does not necessarily result in the N-terminal fusion point being physically closer to the C-terminal fusion point because, for

TABLE 3

Single-Chain I-CreI Meganucleases with Gly-Ser Linkers

| Linker number | N-term. fusion pt. | C-term. fusion pt. | Linker sequence | SEQ ID NO: | Activity | Linker proteolysis |
|---|---|---|---|---|---|---|
| 1 | Val-151 | Phe-9 | $(GSS)_7G$ | 59 | − | − |
| 2 | Val-151 | Phe-9 | $(GSS)_8G$ | 60 | − | − |
| 3 | Val-151 | Phe-9 | $(GSS)_9G$ | 61 | + | + |
| 4 | Val-151 | Phe-9 | $(GSS)_{10}G$ | 62 | ND | +++ |
| 5 | Val-151 | Phe-9 | $(GSS)_{11}G$ | 63 | ND | +++ |
| 6 | Val-151 | Phe-9 | $(GSS)_9GG$ | 64 | + | + |
| 7 | Val-151 | Phe-9 | $(GSS)_9GSG$ | 65 | + | + |
| 8 | Asp-153 | Phe-9 | $(GSS)_9G$ | 61 | + | + |

The results indicated that flexible linkers, such as the Gly-Ser linkers in Table 3, are suitable for single-chain meganuclease production provided that the length is appropriate (see also Example 2). For example, referring to Table 3, single-chain meganucleases including linkers 1 and 2, comprising 22 and 25 total amino acids, respectively, did not exhibit any detectable cleavage activity with the fusion points tested. SDS-PAGE indicated that these meganucleases were intact and were not degraded by proteases, leading to the conclusion that these single-chain meganucleases were structurally stable but functionally constrained by linkers that were too short to allow the individual LAGLIDADG (SEQ ID NO: 55) subunits to adopt the necessary conformation for DNA binding and/or catalysis. Linkers 3, 6, 7, and 8, comprising 28, 29, 30, and 28 amino acids, respectively, all exhibited low levels of cleavage activity. SDS-PAGE indicated that a small amount (5%-10%) of each was proteolyzed into individual subunits while the majority had a molecular weight corresponding to the full-length single-chain meganuclease (~40 example, the N-terminal residues in that region may be part of a secondary/tertiary structure that is pointing either towards or away from the C-terminal fusion point. Thus, moving an N-terminal fusion point in either the N-terminal or C-terminal direction, or moving a C-terminal fusion point in either the N-terminal or C-terminal direction, can result in a shift in the range of acceptable linker lengths toward either longer or shorter linkers. That shift, however, is readily determined, as shown by the experiments reported herein, by routine experimentation and/or three-dimensional modeling.

Thus, in some embodiments, useful flexible linkers have lengths of greater than 25 residues and less than 31 residues (including all values in between), as shown in Table 3 for a single-chain meganuclease based on two I-CreI LAGLIDADG (SEQ ID NO: 55) subunits. In other embodiments, however, employing different LAGLIDADG (SEQ ID NO: 55) subunits and/or different fusion points, useful flexible linkers can have lengths greater than 15 and less than 40 residues (including all values in between), provided that the linkers are not extensively proteolyzed and that the single-chain meganuclease retains DNA-binding and cleavage activity as determined by the simple assays described herein.

2.2.2 Designed, Structured Linkers for Single-Chain Meganucleases

In an effort to produce single-chain I-CreI-based meganucleases with nuclease activity comparable to the natural dimeric enzyme which are both stable enough for long-term storage and resistant to proteolysis, linkers having stable secondary structures can be used to covalently join subunits. A search of the Protein Databank (www.rcsb.org) did not reveal any structurally-characterized LAGLIDADG (SEQ ID NO: 55) proteins with linkers suitable for spanning the great distance (approx. 48 A) between the identified N- and C-terminal fusion points in I-CreI. Therefore, known first principles governing protein structure (e.g., Aurora and Rose (1998), *Protein Sci.* 7:21-38; Fersht, *Structure and Mechanism in Protein Science*, W.H. Freeman 1998) were employed to produce a set of linkers expected to have structural elements suitable for joining the two subunits. Specifically, it was postulated that a suitable linker would comprise (listed from N-terminal fusion point to C-terminal fusion point):

(1) Loop 1.

This structural element starts at the N-terminal fusion point and reverses the direction of the peptide chain back on itself (a 180° turn). The sequence can be 3-8 amino acids and can include at least one glycine residue or, in some embodiments, 2-3 glycines. This structural element can be stabilized by introducing a "C-capping" motif to terminate the C-terminal α-helix of I-CreI and initiate the subsequent turn. The helix cap motif is typically described as beginning with a hydrophobic amino acid in the final turn of the helix (Aurora and Rose (1998), *Protein Sci.* 7:21-38). The C-cap can take any of the forms listed in Table 4:

TABLE 4

| | C-capping Motifs |
|---|---|
| Number | Motif |
| 1 | $h_1$xpx-Gh |
| 2 | $h_1$xpx-nxhx |
| 3 | $h_1$xpx-nxph |
| 4 | $h_1$xxx-Gphx |
| 5 | $h_1$xxx-Gpph |
| 6 | $h_1$xxx-Ppph |
| 7 | $h_1$xxx-Ppph | where h=a hydrophobic amino acid (Ala, Val, Leu, Ile, Met, Phe, Trp, Thr, or Cys); p=a polar amino acid (Gly, Ser, Thr, Asn, Gln, Asp, Glu, Lys, Arg); n=a non-β-branched amino acid (not Val, Ile, Thr, or Pro); x=any amino acid from the h or p group; G=glycine; and P=proline. Note that Thr appears in both groups h and p because its side chain has both hydrophobic (methyl group) and polar (hydroxyl) functional groups. The hyphen designates the end of the α-helix and $h_1$ is a hydrophobic amino acid in the final turn of the helix (i.e., a hydrophobic amino acid 0-4 amino acids prior to the N-terminal fusion point). In the case of I-CreI, $h_1$ is typically Val-151 or Leu-152. Thus, an example of motif 7 is the sequence $V_{151}L_{152}D_{153}$S-PGSV (SEQ ID NO: 66) (see, for example, Table 6, Linker 9).

(2) α-helix 1.

Following Loop 1, this first α-helix in the linker is designed to run anti-parallel to the C-terminal helix in I-CreI (amino acids 144-153) on the outside face of the protein for a distance of approximately 30 Å. This segment should be 10-20 amino acids in length, should not contain any glycine or proline amino acids outside of the N- and C-capping motifs (below), and alternate hydrophobic and polar amino acids with 3-4 amino acid periodicity so as to bury one face of the helix (the hydrophobic face) against the surface of the N-terminal I-CreI subunit while exposing the other face to solvent. The helix could, for example, take the form pphpphhpphpp where p is any polar amino acid and h is any hydrophobic amino acid but neither is glycine or proline such as the sequence SQAS-SAASSASS (SEQ ID NO: 67) (see, for example, Table 6, Linker 9). Numerous algorithms are available to determine the helical propensity of a peptide sequence (e.g., BMERC-PSA, http://bmerc-www.bu.edu/psa/; NNPREDICT, http://alexander.compbio.ucsf.edu/~nomi/nnpredict.html; PredictProtein, http://www.predictprotein.org) and any of these can be used to produce a sequence of the appropriate length that can be expected to adopt α-helical secondary structure. Alternatively, this helix sequence could be derived from a peptide sequence known to adopt α-helical secondary structure in an existing natural or designed protein. Numerous examples of such peptide sequences are available in the Protein Databank (www.rcsb.org).

In addition, it may be desirable to initiate the α-helix with an N-capping motif to stabilize its structure (Aurora and Rose (1998), *Protein Sci.* 7:21-38). This motif spans the loop—α-helix junction and typically has one of the forms shown in Table 5:

TABLE 5

| | N-capping Motifs |
|---|---|
| Number | Motif |
| 1 | h-xpxhx |
| 2 | h-xxpph |
| 3 | hp-xpxhx |
| 4 | hp-xxpph |
| 5 | hpp-xpxhx |
| 6 | hpp-xxpph | where the designations are as in Table 4 above and the hyphen represents the junction between the loop and the helix. An example of motif number 2 is the sequence L-SPSQA (SEQ ID NO: 68) (see, for example, Table 6, Linker 9).

(3) Turn 1.

Following α-helix 1, a short, flexible peptide sequence is introduced to turn the overall orientation of the peptide chain by approximately 90° relative to the orientation of α-helix 1. This sequence can be 3-8 amino acids in length and can contain 1 or, in some embodiments, 2-3 glycines. This sequence can also contain a C-cap such as one of the motifs in Table 4 to stabilize α-helix 1 and initiate the turn. An example is the sequence ASSS-PGSGI (SEQ ID NO: 69) (see, for example, Table 6, Linker 9) which conforms to C-capping motif number 6. In this case, the sequence ASSS (SEQ ID NO: 70) is the final turn of α-helix 1 while the sequence PGSGI (SEQ ID NO: 71) is Turn 1.

(4) α-helix 2.

This helix follows Turn 1 and is designed to lie at the surface of I-CreI in a groove created at the interface between the LAGLIDADG (SEQ ID NO: 55) subunits. The surface of this groove comprises primarily amino acids 94-100 and 134-139 of the N-terminal subunit and amino acids 48-61 of the C-terminal subunit.

α-helix 2 can be designed to be shorter than α-helix 1 and can comprise 1-3 turns of the helix (4-12 amino acids). α-helix 2 can have the same overall amino acid composition as α-helix 1 and can also be stabilized by the addition of an N-capping motif of Table 5. The sequence I-SEALR (SEQ ID NO: 72) is an example (see, for example, Table 6, Linker 9) that conforms to N-capping motif number 1. Linker 9 incorporates a relatively short α-helix 2 comprising the sequence SEALRA (SEQ ID NO: 73) which is expected to make approximately two turns. Experiments with different linker α-helix 2 sequences have demonstrated the importance of helical register in this region of the linker. The addition of a single amino acid (e.g., A, Linker 11), two amino acids (e.g., AS, Linker 12), or three amino acids (e.g., ASS, Linker 13) prior to the termination of α-helix 2 with a glycine amino acid can result in single-chain I-CreI proteins that are unstable and precipitate within moments of purification from *E. coli* (Table 6). In contrast, the addition of four amino acids (e.g., ASSA (SEQ ID NO: 74), linker 14), which is expected to make one full additional turn and restore the helical register to that of Linker 1 is stable and active.

(5) Loop 2.

This loop terminates α-helix 2 and turns the peptide chain back on itself to join with the C-terminal I-CreI subunit at the C-terminal fusion point. As with Loop 1, this sequence can be 3-8 amino acids in length and can contain one or more glycines. It can also contain a C-capping motif from Table 4 to stabilize α-helix 2. For example, the sequence ALRA-GA (SEQ ID NO: 75) from Linker 9 conforms to C-capping motif number 1. In addition, this segment can begin an N-cap on the N-terminal α-helix (amino acids 7-20) of the C-terminal I-CreI subunit. For example the sequence T-KSK$_7$E$_8$F$_9$ (SEQ ID NO: 76) from Linker 9 conforms to N-capping motif number 2. In this instance, the C-terminal fusion point is Lys-7. In other cases, the fusion point can be moved further into the second subunit (for example to amino acids 8 or 9), optionally with the addition of 1-2 amino acids to Loop 2 to compensate for the change in helical register as the C-terminal fusion point is moved. For example, linkers 15-23 in Table 6 below have Glu-8 as the C-terminal fusion point and all have an additional amino acid in Loop 2 relative to Linkers 1-6.

Employing the principles described above, the set of linkers outlined in Table 6 were developed. A set of single-chain I-CreI meganucleases incorporating the linkers between LAM1 and LAM2 subunits was constructed and each was tested for activity against the LAM1/LAM2 hybrid recognition sequence. In all cases, the N-terminal fusion point was Asp-153 of LAM1 and the C-terminal fusion point was either Lys-7 or Glu-8 (denoted in the "CFP" column) of LAM2. Cleavage activity was rated on a four point scale: – no detectable activity; + minimal activity; ++ medium activity; +++ activity comparable to the LAM1/LAM2 heterodimer produced by co-expression of the two monomers in *E. coli* prior to endonuclease purification. Immediately following purification, the single-chain meganucleases were centrifuged (2100g for 10 minutes) to pellet precipitated protein (indicative of structural instability) and the amount of precipitate (ppt) observed was scored: – no precipitate; + slight precipitate; ++ significant precipitate. Those protein samples that precipitated to a significant degree could not be assayed for cleavage activity.

TABLE 6

Linkers for Single-Chain-I-CreI

| # | CFP | Linker Sequence | SEQ ID NO: | Activity | ppt |
|---|-----|-----------------|-----------|----------|-----|
| 9 | K7 | SLPGSVGGLSPSQASSAASSASSSPGSGISEALRAGATKS | 77 | +++ | – |
| 10 | K7 | SLPGSVGGLSPSQASSAASSASSSPGSGISEALRAGGATKS | 78 | +++ | – |
| 11 | K7 | SLPGSVGGLSPSQASSAASSASSSPGSGISEALRAAGGATKS | 79 | ND | ++ |
| 12 | K7 | SLPGSVGGLSPSQASSAASSASSSPGSGISEALRAASGGATKS | 80 | ND | ++ |
| 13 | K7 | SLPGSVGGLSPSQASSAASSASSSPGSGISEALRAASSGGATKS | 81 | ND | ++ |
| 14 | K7 | SLPGSVGGLSPSQASSAASSASSSPGSGISEALRAASSAGGATKS | 82 | +++ | – |
| 15 | E8 | SLPGSVGGLSPSQASSAASSASSSPGSGISEALRAGATKEF | 83 | ++ | + |
| 16 | E8 | SLPGSVGGISPSQASSAASSASSSPGSGTSEAPRAGATKEF | 84 | ++ | – |
| 17 | E8 | SLPGSVGGLSPSQASSAASSASSSPGSGTSEATRAGATKEF | 85 | ++ | + |
| 18 | E8 | SLPGSLGGLSPSQASSAASSASSSPGSGPSEALRAGATKEF | 86 | ++ | + |
| 19 | E8 | SLPGSVGGVSPSQASSAASSASSSPGSGVSEASRAGATKEF | 87 | ++ | + |
| 20 | E8 | SLPGSVGGLSPSQASSAASSASSSPGSGLSEALRAGATKEF | 88 | ++ | + |
| 21 | E8 | SLPGSLGGISPSQASSAASSASSSPGSGSSEASRAGATKEF | 89 | ++ | – |
| 22 | E8 | SPGSVGGVSPSQASSAASSASSSPGSGISEATRAGATKEF | 90 | ++ | – |
| 23 | E8 | SLPGSLGGVSPSQASSAASSPGSGTSEAPRAGATKEF | 91 | ND | ++ |
| 24 | E8 | SLPGSVGGLSPSQASSAASSPGSGISEAIRAGATKEF | 92 | ++ | – |
| 25 | E8 | SLPGSLGGVSPSQASSAASSASSAASSPGSGASEASRAGATKEF | 93 | ++ | – |

Single-chain meganucleases each of these linkers except for 11-13 and 23 (which were not investigated) ran as a single band of the desired molecular weight (~40 kilodaltons) on an SDS-PAGE gel, indicative of resistance to proteolytic cleavage of the linker sequence. In at least one case (Linker 9), the single-chain LAM meganuclease could be stored at 4° C. in excess of 4 weeks without any evidence of degradation or loss of cleavage activity. Moreover, a number of single-chain LAM endonucleases (9, 10, and 14) cleaved the hybrid LAM1/LAM2 recognition sequence with efficiency comparable to the purified LAM1/LAM2 heterodimer, indicating that fusing I-CreI subunits using these linkers does not significantly impair endonuclease activity (see Example 2).

In stark contrast to the purified LAM1/LAM2 heterodimer (which is, in fact, a mixture of homo- and heterodimers), the single-chain LAM meganucleases incorporating the linkers in Table 6 cleave the hybrid site much more efficiently than either of the palindromic sequences (see Example 2). The palindromic sequences are typically cut with <5% efficiency relative to the hybrid site. This unintended cleavage of the palindromic DNA sites could be due to (1) homo-dimerization of LAM1 or LAM2 subunits from a pair of different single-chain proteins, (2) sequential nicking of both strands of the palindromic sequence by a single subunit (LAM1 or LAM2) within the single-chain meganuclease, or (3) minute amounts of homodimeric LAM1 or LAM2 that form following proteolytic cleavage of the single-chain meganuclease into its individual subunits (although SDS-PAGE results make this latter explanation unlikely). Although the single-chain I-CreI meganucleases maintain some activity toward palindromic DNA sites, the activity is so disproportionately skewed in favor of the hybrid site that this approach represents a very significant improvement over existing methods.

3. Single-Chain Meganucleases Derived from I-MsoI

I-MsoI is a close structural homolog of I-CreI and similar methods have been presented for redesigning the DNA-binding specificity of this meganuclease (WO 2007/047859). The method presented above for the production of a single-chain I-CreI meganuclease can be directly applied to I-MsoI. Amino acids Phe-160, Leu-161, and Lys-162 of I-MsoI are structurally homologous to, respectively, Val-151, Leu-152, and Asp-153 of I-CreI. These amino acids, therefore, can be selected as the N-terminal fusion points for I-MsoI. In addition, The X-ray crystal structure of I-MsoI reveals that amino acids 161-166 naturally act as a C-cap and initiate a turn at the C-terminus of the protein which reverses the direction of the peptide chain. Thus, Ile-66 can be selected as the N-terminal fusion point provided that the linker is shortened at its N-terminus to remove the C-cap portion of Loop 1. Pro-9, Thr-10, and Glu-11 of I-MsoI are structurally homologous to, respectively, Lys-7, Glu-8, and Phe-9 of I-CreI and can be selected as C-terminal fusion points for I-MsoI (Table 7). In addition, because the sequence $L_7Q_8P_9T_{10}E_{11}A_{12}$ (SEQ ID NO: 94) of I-MsoI forms a natural N-cap (motif 2 from Table 5), Leu-7 can be included as a fusion point.

TABLE 7

I-MsoI Fusion Points

| N-terminal fusion points | C-terminal fusion points |
|---|---|
| Phe-160 | Leu-7 |
| Leu-161 | Pro-9 |
| Lys-162 | Thr-10 |
| Ile-166 | Glu-11 |

Any of the linkers in Tables 3 or 6 can be used for the production of single-chain I-MsoI endonucleases. For example, Linker 9 from Table 6 may be used to join a pair of I-MsoI subunits into a functional single-chain meganuclease using Lys-162 and Pro-9 as fusion points. In one embodiment, Pro-9 is changed to a different amino acid (e.g., alanine or glycine) because proline is structurally constraining This is analogous to selecting Thr-10 as the C-terminal fusion point and adding an additional amino acid to the C-terminus of the linkers listed in Tables 3 or 6. For example Linkers 26 and 27 from Table 8 are identical to Linker 9 from Table 6 except for the addition of a single amino acid at the C-terminus to account for a change in C-terminal fusion point from Pro-9 (structurally homologous to I-CreI Lys-7) to Thr-10 (structurally homologous to I-CreI Glu-8).

In another embodiment, as described in Example 4, a single-chain meganuclease derived from I-Mso can also be successfully produced using a linker sequence selected from Linker 28-30 from Table 8 in which I-166 is selected as the N-terminal fusion point and Leu-7 is selected as the C-terminal fusion point. Because I-166 is selected as the N-terminal fusion point, the C-cap portion of Loop 1 (corresponding to the first 6 amino acids of each of the linkers from Table 6) can be removed. In addition, α-helix 1 of Linkers 28-30 are lengthened by 3 amino acids (AAS, underlined in Table 8) relative to the linkers listed in Table 6, corresponding to one additional turn of the helix. Using Linkers 28-30 and the specified fusion points, it is possible to produce protease-resistant, high-activity single-chain meganucleases comprising a pair of I-Mso-derived subunits (see Example 4).

TABLE 8

Linkers for Single-Chain I-MsoI

| # | NFP | CFP | Linker Sequence | SEQ ID NO: | Activity | ppt |
|---|---|---|---|---|---|---|
| 26 | K162 | T10 | PGSVGGLSPSQASSAASSASSSPGSGISEALRAGATKSA | 95 | ++ | − |
| 27 | K162 | T10 | PGSVGGLSPSQASSAASSASSSPGSGISEALRAGATKSG | 96 | ++ | − |
| 28 | I166 | L7 | GGASPSQASSAASSASS<u>AAS</u>SPGSGISEALRAASSLASKPGST | 97 | +++ | − |
| 29 | I166 | L7 | GGASPSQASSAASSASS<u>AAS</u>SPGSGISEALRAASSPGST | 98 | +++ | − |
| 30 | I166 | L7 | GGASPSQASSAASSASS<u>AAS</u>SPGSGPSEALRAASSFASKPGST | 99 | +++ | − |

I-CeuI is a close structural homolog of I-CreI and similar methods have been presented for redesigning the DNA-binding specificity of this meganuclease (WO 2007/047859). The method presented above for the production of a single-chain I-CreI meganuclease can be directly applied to I-CeuI. Amino acids Ala-210, Arg-211, and Asn-212 of I-CeuI are structurally homologous to, respectively, Val-151, Leu-152, and Asp-153 of I-CreI. These amino acids, therefore, can be selected as the N-terminal fusion points for I-CeuI. Ser-53, Glu-54, and Ser-55 of I-CeuI are structurally homologous to, respectively, Lys-7, Glu-8, and Phe-9 of I-CreI and can be selected as C-terminal fusion points for I-CeuI (Table 9).

TABLE 9

I-CeuI Fusion Points

| N-terminal fusion points | C-terminal fusion points |
|---|---|
| Ala-210 | Ser-53 |
| Arg-211 | Glu-54 |
| Asn-212 | Ser-55 |

Any of the linkers in Tables 3 or 6 can be effective for the production of single-chain I-CeuI endonucleases. For example, I-CeuI subunits can be joined by Linker 9 from Table 6 using Asn-212 as the N-terminal fusion point and Ser-53 as the C-terminal fusion point.

The C-terminal fusion points selected for I-CeuI result in the removal of amino acids 1-52 from the C-terminal I-CeuI subunit. Structural analyses (Spiegel et al. (2006), *Structure* 14:869-880) reveal that these amino acids form a structured domain that rests on the surface of I-CeuI and buries a substantial amount of hydrophobic surface area contributed by amino acids 94-123. It is possible, therefore, that removing this N-terminal domain will destabilize the C-terminal I-CeuI subunit in the single-chain meganuclease. To mitigate this possibility, the hydrophobic amino acids that would be exposed by the removal of this N-terminal domain can be mutated to polar amino acids (e.g., non-β-branched, hydrophobic amino acids can be mutated to Ser while β-branched, hydrophobic amino acids can be mutated to Thr). For example, Leu-101, Tyr-102, Leu-105, Ala-121, and Leu-123 can be mutated to Ser while Val-95, Val-98, and Ile-113 can be mutated to Thr.

Alternatively, the N-terminal domain of the C-terminal I-CeuI subunit can be left largely intact and joined to the N-terminal subunit via a truncated linker. This can be accomplished using Lys-7, Pro-8, Gly-9, or Glu-10 (SEQ ID NO: 100) as a C-terminal fusion point. The linker can be a flexible Gly-Ser linker (e.g., Linker 3 from Table 3) truncated by approximately 50% of its length (i.e., $(GSS)_4G$ (SEQ ID NO: 101) or $(GSS)_5G$ (SEQ ID NO: 102)). Alternatively, the linker can be any of the linkers from Table 6 truncated within Turn 1. Thus, using Linker 9 from Table 6 as an example, a single-chain I-CeuI meganuclease can be made with the following composition:

```
N-term. subunit
N212-SLPGSVGGLSPSQASSAASSASSSPGS-G9
(SEQ ID NO: 103)
C-term. subunit
```

5. Single-Chain Meganucleases Derived from Two Different LAGLIDADG (SEQ ID NO: 55) Family Members This invention also enables the production of single-chain meganucleases in which each of the subunits is derived from a different natural LAGLIDADG (SEQ ID NO: 55) domain. "Different," as used in this description, refers to LAGLIDADG (SEQ ID NO: 55) subunits that are not derived from the same natural LAGLIDADG (SEQ ID NO: 55) family member. Thus, as used in this description, rationally-designed LAGLIDADG (SEQ ID NO: 55) subunits from the same family member (e.g., two I-CreI subunits that have been genetically engineered with respect to DNA cleavage specificity) are not considered "different". Specifically, the invention enables the production of single-chain meganucleases comprising an N-terminal subunit derived from a mono-LAGLIDADG (SEQ ID NO: 55) meganuclease (e.g., I-CreI, I-MsoI, or I-CeuI) linked to a C-terminal subunit derived from a different mono-LAGLIDADG (SEQ ID NO: 55) meganuclease or either of the two LAGLIDADG (SEQ ID NO: 55) domains from a di-LAGLIDADG (SEQ ID NO: 55) meganuclease. For example, a single-chain meganuclease can be produced comprising an N-terminal I-CreI subunit, which may or may not have been rationally-designed with regard to DNA recognition site specificity, linked to a C-terminal I-MsoI subunit which also may or may not have been rationally-designed with regard to DNA recognition site specificity.

In the cases of I-CreI, I-MsoI, and I-CeuI, the desirable fusion points and linkers are as described above. For example, a single-chain I-CreI to I-MsoI fusion can be produced using Linker 9 from Table 6 to join I-CreI Asp-153 to I-MsoI Thr-10. Table 9 lists potential C-terminal fusion points for individual LAGLIDADG (SEQ ID NO: 55) domains from the di-LAGLIDADG (SEQ ID NO: 55) meganucleases I-SceI, I-DmoI, and I-AniI.

TABLE 10

C-terminal Fusion Points for di-LAGLIDADG Meganuclease Subunits

| I-SceI N-terminal (31-123) | I-SceI C-terminal (132-225) | I-AniI N-terminal (3-125) | I-AniI C-terminal (135-254) | I-DmoI N-terminal (8-98) | I-DmoI C-terminal (104-178) |
|---|---|---|---|---|---|
| I-31 | Y-132 | D3 | S-135 | S-8 | R-104 |
| E-32 | L-133 | L4 | Y-136 | G-9 | E-105 |
| Q-33 | T-134 | Y6 | F-137 | I-10 | Q-106 |

The fusion points listed in Tables 7, 9 and 10 are based on structure comparisons between the meganuclease in question and I-CreI in which amino acid positions which are structurally homologous to the I-CreI fusion points were identified. Fusion points can also be identified in LAGLIDADG (SEQ ID NO: 55) subunits which have not been structurally characterized using protein sequence alignments to I-CreI. This is particularly true of C-terminal fusion points which can be readily identified in any LAGLIDADG (SEQ ID NO: 55) subunit based upon the location of the conserved LAGLIDADG (SEQ NO: 55) motif. The amino acids which are 4-6 residues N-terminal of the start of the LAGLIDADG (SEQ ID NO: 55) motif are acceptable C-terminal fusion points.

Because the dimerization interfaces between subunits from different LAGLIDADG (SEQ ID NO: 55) endonucleases vary, the subunits may not associate into functional "heterodimers" despite being covalently joined as a single polypeptide. To promote association, the interface between the two subunits can be rationally-designed, as described in WO 2007/047859. At its simplest, this involves substituting interface residues from one subunit onto another. For example, I-CreI and I-MsoI differ in the interface region primarily at I-CreI Glu-8 (which is a Thr in the homologous position of I-MsoI, amino acid 10) and Leu-11 (which is an Ala in the homologous position of I-MsoI, amino acid 13). Thus, I-CreI and I-MsoI subunits can be made to interact effectively by changing Glu-8 and Leu-11 of the 1-CreI subunit to Thr and Ala, respectively, or by changing Thr-10 and Ala-13 of the I-MsoI subunit to Glu and Leu, respectively.

Techniques such as computational protein design algorithms can also be used to rationally-design the subunit interfaces. Such methods are known in the art. For example, Chevalier et al. used a computational algorithm to redesign the interface between I-CreI and the N-terminal LAGLIDADG (SEQ ID NO: 55) domain of I-DmoI to enable the two to interact (Chevalier et al. (2002), *Mol. Cell.* 10:895-905). Taking these results into account, a single-chain meganuclease comprising an N-terminal subunit derived from I-CreI and a C-terminal subunit derived from the N-terminal LAGLIDADG (SEQ ID NO: 55) domain of I-DmoI can be produced by (1) selecting an N-terminal fusion point in I-CreI from Table 2, (2) selecting a C-terminal fusion point in I-DmoI from Table 10, (3) selecting a linker from Table 6 (or designing a similar linker based on the rules provided), and (4) incorporating the mutations L11A, F16I, K96N, and L97F into the I-CreI subunit and the mutations I19W, H51F, and L55R into the I-DmoI subunit as proposed by Chevalier et al.

Alternatively, empirical methods such as directed evolution can be used to engineer the interface between two different LAGLIDADG (SEQ ID NO: 55) subunits. Such methods are known in the art. For example, genetic libraries can be produced in which specific amino acids in the subunit interface are randomized, and library members which permit the interaction between the two subunits are screened experimentally. Such screening methods are known in the art (e.g., Sussman et al. (2004), *J. Mol. Biol.* 342: 31-41; Chames et al. (2005), *Nucl. Acids Res.* 33: e178; Seligman et al. (2002), *Nucl. Acids Res.* 30: 3870-9, Arnould et al. (2006), *J Mol, Biol.* 355: 443-58) and can be conducted to test for the ability of a single-chain meganuclease comprising two different LAGLIDADG (SEQ ID NO: 55) subunits to cleave a hybrid DNA site within a yeast or bacterial cell.

6. Single-Chain Meganucleases with Altered DNA-Cleavage Specificity, Activity, and/or DNA-Binding Affinity The invention can be used to produce single-chain meganucleases comprising individual LAGLIDADG (SEQ ID NO: 55) subunits that have been genetically-engineered with respect to DNA-cleavage specificity using a variety of methods. Such methods include rational-design (e.g., WO 2007/047859), computational design (e.g., Ashworth et al. (2006), *Nature* 441:656-659), and genetic selection (Sussman et al. (2004), *J Mol, Biol.* 342: 31-41; Chames et al. (2005), *Nucl. Acids Res.* 33: e178; Seligman et al. (2002), *Nucl. Acids Res.* 30: 3870-9, Arnould et al. (2006), *J. Mol. Biol.* 355: 443-58). Such meganucleases can be targeted to DNA sites that differ from the sites recognized by wild-type meganucleases. The invention can also be used to join LAGLIDADG (SEQ ID NO: 55) subunits that have been rationally-designed to have altered activity (e.g., WO 2007/047859; Arnould et al (2007), *J. Biol* 371 (1):49-65) or DNA-binding affinity as described in WO 2007/047859.

7. Methods of Producing Recombinant Cells and Organisms

Aspects of the present invention further provide methods for producing recombinant, transgenic or otherwise genetically-modified cells and organisms using single-chain meganucleases. Thus, in certain embodiments, recombinant single-chain meganucleases are developed to specifically cause a double-stranded break at a single site or at relatively few sites in the genomic DNA of a cell or an organism to allow for precise insertion(s) of a sequence of interest by homologous recombination. In other embodiments, recombinant meganucleases are developed to specifically cause a double-stranded break at a single site or at relatively few sites in the genomic DNA of a cell or an organism to either (a) allow for rare insertion(s) of a sequence of interest by non-homologous end joining or (b) allow for the disruption of the target sequence by non-homologous end joining As used herein with respect to homologous recombination or non-homologous end joining of sequences of interest, the term "insertion" means the ligation of a sequence of interest into a chromosome such that the sequence of interest is integrated into the chromosome. In the case of homologous recombination, an inserted sequence can replace an endogenous sequence, such that the original DNA is replaced by exogenous DNA of equal length, but with an altered nucleotide sequence. Alternatively, an inserted sequence can include more or fewer bases than the sequence it replaces.

Therefore, in accordance with this aspect of the invention, the recombinant organisms include, but are not limited to, monocot plant species such as rice, wheat, corn (maize) and rye, and dicot species such as legumes (e.g., kidney beans, soybeans, lentils, peanuts, peas), alfalfa, clover, tobacco and *Arabidopsis* species. In addition, the recombinant organisms can include, but are not limited to, animals such as humans and non-human primates, horses, cows, goats, pigs, sheep, dogs, cats, guinea pigs, rats, mice, lizards, fish and insects such as *Drosophila* species. In other embodiments, the organism is a fungus such as a *Candida*, *Neurospora* or *Saccharomyces* species.

In some embodiments, the methods of the invention involve the introduction of a sequence of interest into a cell such as a germ cell or stem cell that can become a mature recombinant organism or allow the resultant genetically-modified organism to give rise to progeny carrying the inserted sequence of interest in its genome.

Meganuclease proteins can be delivered into cells to cleave genomic DNA, which allows for homologous recombination or non-homologous end joining at the cleavage site with a sequence of interest, by a variety of different mechanisms known in the art. For example, the recombinant meganuclease protein can introduced into a cell by techniques including, but not limited to, microinjection or liposome transfections (see, e.g., Lipofectamine™, Invitrogen Corp., Carlsbad, Calif.). The liposome formulation can be used to facilitate lipid bilayer fusion with a target cell, thereby allowing the contents of the liposome or proteins associated with its surface to be brought into the cell. Alternatively, the enzyme can be fused to an appropriate uptake peptide such as that from the HIV TAT protein to direct cellular uptake (see, e.g., Hudecz et al. (2005), *Med. Res. Rev.* 25: 679-736).

Alternatively, gene sequences encoding the meganuclease protein are inserted into a vector and transfected into a eukaryotic cell using techniques known in the art (see, e.g., Ausubel et. al., *Current Protocols in Molecular Biology*, Wiley 1999). The sequence of interest can be introduced in the same vector, a different vector, or by other means known in the art.

Non-limiting examples of vectors for DNA transfection include virus vectors, plasmids, cosmids, and YAC vectors. Transfection of DNA sequences can be accomplished by a variety of methods known to those of skill in the art. For instance, liposomes and immunoliposomes are used to deliver DNA sequences to cells (see, e.g., Lasic et al. (1995), *Science* 267: 1275-76). In addition, viruses can be utilized to introduce vectors into cells (see, e.g., U.S. Pat. No. 7,037,492). Alternatively, transfection strategies can be utilized such that the vectors are introduced as naked DNA (see, e.g., Rui et al. (2002), *Life Sci.* 71(15): 1771-8).

General methods for delivering nucleic acids into cells include: (1) chemical methods (Graham et al. (1973), *Virology* 54(2):536-539; Zatloukal et al. (1992), *Ann. N.Y. Acad. Sci.,* 660:136-153; (2) physical methods such as microinjection (Capecchi (1980), *Cell* 22(2):479-488, electroporation (Wong et al. (1982), *Biochim. Biophys. Res. Commun.* 107 (2):584-587; Fromm et al. (1985), *Proc. Nat'l Acad. Sci. USA* 82(17):5824-5828; U.S. Pat. No. 5,384,253) and ballistic injection (Johnston et al. (1994), *Methods Cell. Biol.* 43(A): 353-365; Fynan et al. (1993), *Proc. Nat'l Acad. Sci. USA* 90(24): 11478-11482); (3) viral vectors (Clapp (1993), *Clin. Perinatol.* 20(1): 155-168; Lu et al. (1993), *J. Exp. Med.* 178(6):2089-2096; Eglitis et al. (1988), *Avd. Exp. Med. Biol.* 241:19-27; Eglitis et al. (1988), *Biotechniques* 6(7):608-614); and (4) receptor-mediated mechanisms (Curiel et al. (1991), *Proc. Nat'l Acad. Sci. USA* 88(19):8850-8854; Curiel et al. (1992), *Hum. Gen. Ther.* 3(2):147-154; Wagner et al. (1992), *Proc. Nat'l Acad. Sci. USA* 89 (13): 6099-6103).

In certain embodiments, a genetically-modified plant is produced, which contains the sequence of interest inserted into the genome. In certain embodiments, the genetically-modified plant is produced by transfecting the plant cell with DNA sequences corresponding to the recombinant meganuclease and the sequence of interest, which may or may not be flanked by the meganuclease recognition sequences and/or sequences substantially identical to the target sequence. In other embodiments, the genetically-modified plant is produced by transfecting the plant cell with DNA sequences corresponding to the recombinant meganuclease only, such that cleavage promotes non-homologous end joining and disrupts the target sequence containing the recognition sequence. In such embodiments, the meganuclease sequences are under the control of regulatory sequences that allow for expression of the meganuclease in the host plant cells. These regulatory sequences include, but are not limited to, constitutive plant promoters such as the NOS promoter, chemically-inducible gene promoters such as the dexamethasone-inducible promoter (see, e.g., Gremillon et al. (2004), *Plant J.* 37:218-228), and plant tissue specific promoters such as the LGC1 promoter (see, e.g., Singh et al. (2003), FEBS Lett. 542:47-52).

Suitable methods for introducing DNA into plant cells include virtually any method by which DNA can be introduced into a cell, including but not limited to *Agrobacterium* infection, PEG-mediated transformation of protoplasts (Omirulleh et al. (1993), *Plant Molecular Biology,* 21:415-428), desiccation/inhibition-mediated DNA uptake, electroporation, agitation with silicon carbide fibers, ballistic injection or microprojectile bombardment, and the like.

In other embodiments, a genetically-modified animal is produced using a recombinant meganuclease. As with plant cells, the nucleic acid sequences can be introduced into a germ cell or a cell that will eventually become a transgenic organism. In some embodiments, the cell is a fertilized egg, and exogenous DNA molecules can be injected into the pronucleus of the fertilized egg. The micro-injected eggs are then transferred into the oviducts of pseudopregnant foster mothers and allowed to develop. The recombinant meganuclease is expressed in the fertilized egg (e.g., under the control of a constitutive promoter, such as 3-phosphoglycerate kinase), and facilitates homologous recombination of the sequence of interest into one or a few discrete sites in the genome. Alternatively, the genetically-modified animals can be obtained by utilizing recombinant embryonic stem ("ES") cells for the generation of the transgenics, as described by Gossler et al. (1986), *Proc. Natl. Acad. Sci. USA* 83:9065 9069.

In certain embodiments, a recombinant mammalian expression vector is capable of directing tissue-specific expression of the nucleic acid preferentially in a particular cell type. Tissue-specific regulatory elements are known in the art. Non-limiting examples of suitable tissue-specific promoters include the albumin promoter (liver-specific; Pinkert et al. (1987), *Genes Dev.* 1: 268-277), lymphoid-specific promoters (Calame and Eaton (1988), *Adv. Immunol.* 43: 235-275), in particular promoters of T cell receptors (Winoto and Baltimore (1989), *EMBO J.* 8: 729-733) and immunoglobulins (Banerji et al. (1983), *Cell* 33: 729-740; Queen and Baltimore (1983), *Cell* 33: 741-748), neuron-specific promoters (e.g., the neurofilament promoter; Byrne and Ruddle (1989), *Proc. Natl. Acad. Sci. USA* 86: 5473-5477), pancreas-specific promoters (Edlund et al. (1985), *Science* 230: 912-916), and mammary gland-specific promoters (e.g., milk whey promoter; U.S. Pat. No. 4,873,316 and European Pat. Pub. EP 0 264 166). Developmentally-regulated promoters are also encompassed, e.g., the murine hox promoters (Kessel and Gruss (1990), *Science* 249: 374-379) and the α-fetoprotein promoter (Campes and Tilghman (1989), *Genes Dev.* 3: 537-546).

In certain embodiments, a single-chain meganuclease may be tagged with a peptide epitope (e.g., an HA, FLAG, or Myc epitope) to monitor expression levels or localization. In some embodiments, the meganuclease may be fused to a sub-cellular localization signal such as a nuclear-localization signal (e.g., the nuclear localization signal from SV40) or chloroplast or mitochondrial localization signals. In other embodiments, the meganuclease may be fused to a nuclear export signal to localize it to the cytoplasm. The meganuclease may also be fused to an unrelated protein or protein domain such as a protein that stimulates DNA-repair or homologous recombination (e.g., recA, RAD51, RAD52, RAD54, RAD57 or BRCA2).

8. Methods for Gene Therapy

Aspects of the invention allow for the use of recombinant meganuclease for gene therapy. As used herein, "gene therapy" means therapeutic treatments that comprise introducing into a patient a functional copy of at least one gene, or gene regulatory sequence such as a promoter, enhancer, or silencer to replace a gene or gene regulatory region that is defective in its structure and/or function. The term "gene therapy" can also refer to modifications made to a deleterious gene or regulatory element (e.g., oncogenes) that reduce or eliminate expression of the gene. Gene therapy can be performed to treat congenital conditions, conditions resulting from mutations or damage to specific genetic loci over the life of the patient, or conditions resulting from infectious organisms.

In some aspects of the invention, dysfunctional genes are replaced or disabled by the insertion of exogenous nucleic acid sequences into a region of the genome affecting gene expression. In certain embodiments, the recombinant meganuclease is targeted to a particular sequence in the region of the genome to be modified so as to alleviate the condition. The sequence can be a region within an exon, intron, promoter, or other regulatory region that is causing dysfunctional expression of the gene. As used herein, the term "dysfunctional expression" means aberrant expression of a gene product either by the cell producing too little of the gene product, too much of the gene product, or producing a gene product that has a different function such as lacking the necessary function or having more than the necessary function.

Exogenous nucleic acid sequences inserted into the modified region can be used to provide "repaired" sequences that normalize the gene. Gene repair can be accomplished by the introduction of proper gene sequences into the gene allowing for proper function to be reestablished. In these embodiments, the nucleic acid sequence to be inserted can be the entire coding sequence for a protein or, in certain embodiments, a fragment of the gene comprising only the region to be repaired. In other embodiments the nucleic acid sequence to be inserted comprises a promoter sequence or other regulatory elements such that mutations causing abnormal expression or regulation are repaired. In other embodiments, the nucleic acid sequence to be inserted contains the appropriate translation stop codon lacking in a mutated gene. The nucleic acid sequence can also have sequences for stopping transcription in a recombinant gene lacking appropriate transcriptional stop signals.

Alternatively, the nucleic acid sequences can eliminate gene function altogether by disrupting the regulatory sequence of the gene or providing a silencer to eliminate gene function. In some embodiments, the exogenous nucleic acid sequence provides a translation stop codon to prevent expression of the gene product. In other embodiments, the exogenous nucleic acid sequences provide transcription stop element to prevent expression of a full length RNA molecule. In still other embodiments, gene function is disrupted directly by the meganuclease by introducing base insertions, base deletions, and/or frameshift mutations through non-homologous end-joining.

In many instances, it is desirable to direct the proper genetic sequences to a target cell or population of cells that is the cause of the disease condition. Such targeting of therapeutics prevents healthy cells from being targeted by the therapeutics. This increases the efficacy of the treatment, while decreasing the potentially adverse effects that the treatment could have on healthy cells.

Delivery of recombinant meganuclease genes and the sequence of interest to be inserted into the genome to the cells of interest can be accomplished by a variety of mechanisms. In some embodiments, the nucleic acids are delivered to the cells by way of viruses with particular viral genes inactivated to prevent reproduction of the virus. Thus, a virus can be altered so that it is capable only of delivery and maintenance within a target cell, but does not retain the ability to replicate within the target cell or tissue. One or more DNA sequences can be introduced to the altered viral genome, so as to produce a viral genome that acts like a vector, and may or may not be inserted into a host genome and subsequently expressed. More specifically, certain embodiments include employing a retroviral vector such as, but not limited to, the MFG or pLJ vectors. An MFG vector is a simplified Moloney murine leukemia virus vector (MoMLV) in which the DNA sequences encoding the pol and env proteins have been deleted to render it replication defective. A pLJ retroviral vector is also a form of the MoMLV (see, e.g., Korman et al. (1987), *Proc. Nat'l Acad. Sci.*, 84:2150-2154). In other embodiments, a recombinant adenovirus or adeno-associated virus can be used as a delivery vector.

In other embodiments, the delivery of recombinant meganuclease protein and/or recombinant meganuclease gene sequences to a target cell is accomplished by the use of liposomes. The production of liposomes containing nucleic acid and/or protein cargo is known in the art (see, e.g., Lasic et al. (1995), *Science* 267: 1275-76). Immunoliposomes incorporate antibodies against cell-associated antigens into liposomes, and can delivery DNA sequences for the meganuclease or the meganuclease itself to specific cell types (see, e.g., Lasic et al. (1995), *Science* 267: 1275-76; Young et al. (2005), *J. Calif. Dent. Assoc.* 33(12): 967-71; Pfeiffer et al. (2006), *J. Vasc. Surg.* 43(5):1021-7). Methods for producing and using liposome formulations are well known in the art, (see, e.g., U.S. Pat. No. 6,316,024, U.S. Pat. No. 6,379,699, U.S. Pat. No. 6,387,397, U.S. Pat. No. 6,511,676 and U.S. Pat. No. 6,593,308, and references cited therein). In some embodiments, liposomes are used to deliver the sequences of interest as well as the recombinant meganuclease protein or recombinant meganuclease gene sequences.

9. Methods for Treating Pathogen Infection

Aspects of the invention also provide methods of treating infection by a pathogen. Pathogenic organisms include viruses such as, but not limited to, herpes simplex virus 1, herpes simplex virus 2, human immunodeficiency virus 1, human immunodeficiency virus 2, variola virus, polio virus, Epstein-Barr virus, and human papilloma virus and bacterial organisms such as, but not limited to, *Bacillus anthracis, Haemophilus* species, *Pneumococcus* species, *Staphylococcus aureus, Streptococcus* species, methicillin-resistant *Staphylococcus aureus*, and *Mycoplasma tuberculosis*. Pathogenic organisms also include fungal organisms such as, but not limited to, *Candida, Blastomyces, Cryptococcus*, and *Histoplasma* species.

In some embodiments, a single-chain meganuclease can be targeted to a recognition sequence within the pathogen genome, e.g., to a gene or regulatory element that is essential for growth, reproduction, or toxicity of the pathogen. In certain embodiments, the recognition sequence may be in a bacterial plasmid. Meganuclease-mediated cleavage of a recognition sequence in a pathogen genome can stimulate mutation within a targeted, essential gene in the form of an insertion, deletion or frameshift, by stimulating non-homologous end-joining Alternatively, cleavage of a bacterial plasmid can result in loss of the plasmid along with any genes encoded on it, such as toxin genes (e.g., *B. anthracis* Lethal Factor gene) or antibiotic resistance genes. As noted above, the meganuclease may be delivered to the infected patient, animal, or plant in either protein or nucleic acid form using techniques that are common in the art. In certain embodiments, the meganuclease gene may be incorporated into a bacteriophage genome for delivery to pathogenic bacteria.

Aspects of the invention also provide therapeutics for the treatment of certain forms of cancer. Because human viruses are often associated with tumor formation (e.g., Epstein-Barr Virus and nasopharyngeal carcinomas; Human Papilloma Virus and cervical cancer) inactivation of these viral pathogens may prevent cancer development or progression. Alternatively, double-stranded breaks targeted to the genomes of these tumor-associated viruses using single-chain meganucleases may be used to trigger apoptosis through the DNA damage response pathway. In this manner, it may be possible to selectively induce apoptosis in tumor cells harboring the viral genome.

10. Methods for Genotyping and Pathogen Identification

Aspects of the invention also provide tools for in vitro molecular biology research and development. It is common in the art to use site-specific endonucleases (e.g., restriction enzymes) for the isolation, cloning, and manipulation of nucleic acids such as plasmids, PCR products, BAC sequences, YAC sequences, viruses, and genomic sequences from eukaryotic and prokaryotic organisms (see, e.g., Ausubel et al., Current Protocols in Molecular Biology, Wiley 1999). Thus, in some embodiments, a single-chain meganuclease may be used to manipulate nucleic acid sequences in vitro. For example, single-chain meganucleases recognizing a pair of recognition sequences within the same DNA molecule can be used to isolate the intervening DNA segment for subsequent manipulation such as ligation into a bacterial plasmid, BAC, or YAC.

In another aspect, this invention provides tools for the identification of pathogenic genes and organisms. In one embodiment, single-chain meganucleases can be used to cleave recognition sites corresponding to polymorphic genetic regions correlated to disease to distinguish disease-causing alleles from healthy alleles (e.g., a single-chain meganuclease which recognizes the ΔF-508 allele of the human CFTR gene, see example 4). In this embodiment, DNA sequences isolated from a human patient or other organism are digested with a single-chain meganuclease, possibly in conjunction with additional site-specific nucleases, and the resulting DNA fragment pattern is analyzed by gel electrophoresis, capillary electrophoresis, mass spectrometry, or other methods known in the art. This fragmentation pattern and, specifically, the presence or absence of cleavage by the single-chain meganuclease, indicates the genotype of the organism by revealing whether or not the recognition sequence is present in the genome. In another embodiment, a single-chain meganuclease is targeted to a polymorphic region in the genome of a pathogenic virus, fungus, or bacterium and used to identify the organism. In this embodiment, the single-chain meganuclease cleaves a recognition sequence that is unique to the pathogen (e.g., the spacer region between the 16S and 23S rRNA genes in a bacterium; see, e.g., van der Giessen et al. (1994), *Microbiology* 140: 1103-1108) and can be used to distinguish the pathogen from other closely-related organisms following endonuclease digest of the genome and subsequent analysis of the fragmentation pattern by electrophoresis, mass spectrometry, or other methods known in the art.

11. Methods for the Production of Custom DNA-Binding Domains

In another aspect, the invention provides single-chain DNA-binding proteins that lack endonuclease cleavage activity. The catalytic activity of a single-chain meganuclease can be eliminated by mutating amino acids involved in catalysis (e.g., the mutation of Q47 to E in I-CreI, see Chevalier et al. (2001), *Biochemistry.* 43:14015-14026); the mutation of D44 or D145 to N in I-SceI; the mutation of E66 to Q in I-CeuI; the mutation of D22 to N in I-MsoI). The inactivated meganuclease can then be fused to an effector domain from another protein including, but not limited to, a transcription activator (e.g., the GAL4 transactivation domain or the VP16 transactivation domain), a transcription repressor (e.g., the KRAB domain from the Kruppel protein), a DNA methylase domain (e.g., M.CviPI or M.SssI), or a histone acetyltransferase domain (e.g., HDAC1 or HDAC2). Chimeric proteins consisting of an engineered DNA-binding domain, most notably an engineered zinc finger domain, and an effector domain are known in the art (see, e.g., Papworth et al. (2006), *Gene* 366:27-38).

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below. Example 1 presents evidence that a previously disclosed method for the production of single-chain I-CreI meganucleases (Epinat et al. (2003), *Nucleic Acids Res.* 31: 2952-62; WO 2003/078619) is not sufficient for the production of meganucleases recognizing non-palindromic DNA sites, Examples 2 and 3 present evidence that the method described here is sufficient to produce single-chain I-CreI meganucleases recognizing non-palindromic DNA sites using a flexible Gly-Ser linker (example 2) or a designed, structured linker (example 3). Although examples 2 and 3 below refer specifically to single-chain meganucleases based on I-CreI, single-chain meganucleases comprised of subunits derived from I-SceI, I-MsoI, I-CeuI, I-AniI, and other LAGLIDADG (SEQ ID NO: 55) meganucleases can be similarly produced and used, as described herein.

Example 1

Evaluation of the Method of Epinat et al.

1. Single Chain Meganucleases Using the Method of Epinat et al.

Epinat et al. (2003), *Nucleic Acids Res.* 31: 2952-62 and WO 2003/078619 report the production of a single-chain meganuclease derived from the I-CreI meganuclease. Specifically, the authors used an 11 amino acid peptide linker derived from I-DmoI (amino acids 94-104 of I-DmoI, sequence MLERIRLFNMR (SEQ ID NO: 104)) to join an N-terminal I-CreI subunit (amino acids 1-93 of I-CreI) to a C-terminal I-CreI subunit (amino acids 8-163). This particular arrangement of N-terminal subunit—linker—C-terminal subunit was selected because it most closely mimics the domain organization of the di-LAGLIDADG (SEQ ID NO: 55) I-DmoI meganuclease. The authors evaluated the single-chain I-CreI meganuclease experimentally and found it to cleave a wild-type I-CreI recognition sequence effectively, albeit at a significantly reduced rate relative to the wild-type I-CreI homodimer.

Because the fusion protein produced by these authors comprised two otherwise wild-type subunits, both of which recognize identical DNA half-sites, it was necessary to test the single-chain meganuclease using the pseudo-palindromic wild-type DNA site. As such, it was not possible for the authors to rule out the possibility that the observed cleavage activity was not due to cleavage by an individual single-chain meganuclease but, rather, by a intermolecular dimer of two single-chain meganucleases in which one domain from each associated to form a functional meganuclease that effectively behaves like the wild-type homodimer. Indeed, a substantial portion of the N-terminal I-CreI subunit (amino acids 94-163) was removed in the production of the single-chain meganuclease reported by Epinat et al. An inspection of the three-dimensional I-CreI crystal structure (Jurica et al. (1998), *Mol. Cell.* 2:469-476) reveals that this truncation results in the removal of three alpha-helices from the surface of the N-terminal subunit and the subsequent exposure to solvent of a significant amount of hydrophobic surface area. As such, the present inventors hypothesized that the N-terminal subunit from the single-chain I-CreI meganuclease of Epinat et al. is unstable and inactive and that the observed DNA cleavage activity is, in fact, due to the dimerization of the C-terminal subunits from two single-chain proteins. The protein stability problems resulting from application of the method of Epinat et al. are also discussed in Fajardo-Sanchez et al. (2008), *Nucleic Acids Res.* 36:2163-2173.

2. Design of Single-Chain LAM Meganucleases Using the Method of Epinat et al.

To more critically evaluate the method for single-chain I-CreI meganuclease production reported by Epinat et al. (Epinat et al. (2003), *Nucleic Acids Res.* 31: 2952-62; WO 2003/078619), a single-chain meganuclease was produced in which the N- and C-terminal I-CreI domains recognize different DNA half-sites. The method reported in Epinat et al. was used to produce a pair of single-chain meganucleases comprising one LAM1 domain and one LAM2 domain. This "LAM1epLAM2" meganuclease (SEQ ID NO: 48) comprises an N-terminal LAM1 domain and a C-terminal LAM2 domain while "LAM2epLAM1" (SEQ ID NO: 49) comprises an N-terminal LAM2 domain and a C-terminal LAM1 domain. In total, both single-chain meganucleases differ by 11 amino acids from that reported by Epinat et al. and all amino acid changes are in regions of the enzyme responsible for DNA recognition which are not expected to affect subunit interaction.

3. Construction of Single-Chain Meganucleases

LAM1epLAM2 and LAM2epLAM1 were produced by PCR of existing LAM1 and LAM2 genes with primers that introduce the I-DmoI linker sequence (which translates to MLERIRLFNMR (SEQ ID NO: 104)) as well as restriction enzyme sites for cloning. The two LAM subunits were cloned sequentially into pET-21a vectors with a six histidine tag (SEQ ID NO: 110) fused at the 3' end of the full-length single-chain gene for purification (Novagen Corp., San Diego, Calif.). All nucleic acid sequences were confirmed using Sanger Dideoxynucleotide sequencing (see, Sanger et al. (1977), *Proc. Natl. Acad. Sci. USA.* 74(12): 5463-7).

The LAMep meganucleases were expressed and purified using the following method. The constructs cloned into a pET21a vector were transformed into chemically competent BL21 (DE3) pLysS, and plated on standard 2×YT plates containing 200 µg/ml carbanicillin. Following overnight growth, transformed bacterial colonies were scraped from the plates and used to inoculate 50 ml of 2×YT broth. Cells were grown at 37° C. with shaking until they reached an optical density of 0.9 at a wavelength of 600 nm. The growth temperature was then reduced from 37° C. to 22° C. Protein expression was induced by the addition of 1 mM IPTG, and the cells were incubated with agitation for two and a half hours. Cells were then pelleted by centrifugation for 10 min. at 6000×g. Pellets were resuspended in 1 ml binding buffer (20 mM Tris-HCL, pH 8.0, 500 mM NaCl, 10 mM imidazole) by vortexing. The cells were then disrupted with 12 pulses of sonication at 50% power and the cell debris was pelleted by centrifugation for 15 min at 14,000×g. Cell supernatants were diluted in 4 ml binding buffer and loaded onto a 200 µl nickel-charged metal-chelating Sepharose column (Pharmacia).

The column was subsequently washed with 4 ml wash buffer (20 mM Tris-HCl, pH 8.0, 500 mM NaCl, 60 mM imidazole) and with 0.2 ml elution buffer (20 mM Tris-HCl, pH 8.0, 500 mM NaCl, 400 mM imidazole). Meganuclease enzymes were eluted with an additional 0.6 ml of elution buffer and concentrated to 50-130 µl using Vivospin disposable concentrators (ISC, Inc., Kaysville, Utah). The enzymes were exchanged into SA buffer (25 mM Tris-HCL, pH 8.0, 100 mM NaCl, 5 mM $MgCl_2$, 5 mM EDTA) for assays and storage using Zeba spin desalting columns (Pierce Biotechnology, Inc., Rockford, Ill.). The enzyme concentration was determined by absorbance at 280 nm using an extinction coefficient of 23,590 $M^{-1}cm^{-1}$. Purity and molecular weight of the enzymes was then confirmed by MALDI-TOF mass spectrometry.

4. Cleavage Assays

All enzymes purified as described above were assayed for activity by incubation with linear, double-stranded DNA substrates containing meganuclease recognition sequences. Synthetic oligonucleotides corresponding to both sense and antisense strands of the recognition sequences were annealed and were cloned into the SmaI site of the pUC19 plasmid by blunt-end ligation. The sequences of the cloned binding sites were confirmed by Sanger dideoxynucleotide sequencing. All plasmid substrates were linearized with XmnI or ScaI concurrently with the meganuclease digest. The enzyme digests contained 5 µl 0.05 µM DNA substrate, 2.5 µl 5 µM single-chain meganuclease, 9.5 µl SA buffer, and 0.5 µl XmnI or ScaI. Digests were incubated at either 37° C. for four hours. Digests were stopped by adding 0.3 mg/ml Proteinase K and 0.5% SDS, and incubated for one hour at 37° C. Digests were analyzed on 1.5% agarose and visualized by ethidium bromide staining.

5. Results

The LAMep meganucleases produced using the method of Epinat et al. were incubated with DNA substrates comprising the LAM1 palindrome (SEQ ID NOs: 40 and 41), the LAM2 palindrome (SEQ ID NOs: 44 and 45), or the LAM1/LAM2 hybrid site (SEQ ID NOs: 46 and 47). The LAM1epLAM2 single-chain meganuclease was found to cleave primarily the LAM2 palindrome whereas the LAM2epLAM1 single-chain meganuclease was found to cleave primarily the LAM1 palindrome. Neither single-chain meganuclease cleaved the hybrid site to a significant degree. These results suggest that, indeed, the method of Epinat et al. produces single-chain meganucleases that are unable to cleave non-palindromic DNA sequences. Both single-chain meganucleases were found to cleave primarily the recognition sequence corresponding to a palindrome of the half-site recognized by the C-terminal subunit, suggesting that the N-terminal subunit is inactive. Thus, the active meganuclease species characterized by Epinat et al. appears to be primarily a dimer between the C-terminal subunits of a pair of single-chain I-CreI meganucleases. Alternatively, cleavage of the palindromic DNA site may be due to sequential single strand nicking by the C-terminal subunits of different single-chain I-CreI meganucleases. In either case, in contrast to claims made by Epinat et al., the method does not produce a substantially functional single-chain I-CreI heterodimer and is generally not useful for the recognition and cleavage of non-palindromic DNA sites.

Example 2

Single-Chain I-CreI Meganucleases Produced Using a Flexible Gly-Ser Linker

1. Design of Single-Chain LAM Meganucleases Using a Gly-Ser Linker

The designed LAM1 and LAM2 endonucleases were fused into a single polypeptide using Linker 3 from Table 3. Val-151 was used as the N-terminal fusion point (to the LAM1 subunit) while Phe-9 was the C-terminal fusion point (to the LAM2 subunit). The resulting single-chain meganuclease, "LAM1gsLAM2" (SEQ ID NO: 50) was cloned into pET21a, expressed in *E. coli* and purified as described in Example 1.

2. Results

LAM1gsLAM2 was assayed for cleavage activity using the same DNA substrates and incubation conditions as described in Example 1. In contrast to results with the LAMep meganucleases, LAM was found to cleave primarily the hybrid LAM1/LAM2 recognition sequence (SEQ ID NOs: 46 and 47). The extent of cleavage is significantly reduced relative to the LAM1/LAM2 heterodimer produced by co-expressing the LAM1 and LAM2 monomers in *E. coli*. Under the same reaction conditions, the heterodimer cleaves the LAM1/LAM2 recognition sequence to completion, suggesting that the Gly-Ser linker impairs cleavage activity to some extent. Nonetheless, LAM1gsLAM2 exhibits a much stronger preference for the hybrid site over the palindromic LAM1 or LAM2 sites and, so has utility for applications in which specificity is of greater importance than activity.

Example 3

Single-Chain I-CreI Meganucleases Produced Using a Structured Linker

1. Design of Single-Chain LAM Meganucleases Using a Designed, Structured Linker

The designed LAM1 and LAM2 endonucleases were fused into a single polypeptide using Linker 9 from Table 6. Asp-153 was used as the N-terminal fusion point (to the LAM1 subunit) while Lys-7 was the C-terminal fusion point (to the LAM2 subunit). The resulting single-chain meganuclease, "LAM1desLAM2" (SEQ ID NO: 51) was cloned into pET21a, expressed in *E. coli* and purified as described in Example 1.

2. Results

LAM1desLAM2 was assayed for cleavage activity using the same DNA substrates and incubation conditions as described in Example 1. In contrast to results with the LAMep meganucleases, LAM1desLAM2 was found to cleave primarily the hybrid LAM1/LAM2 recognition sequence (SEQ ID NO: 46 and 47). The extent of cleavage is comparable to the LAM1/LAM2 heterodimer produced by co-expressing the LAM1 and LAM2 monomers in *E. coli*. These results suggest that designed, structured linkers such as Linker 9 do not interfere significantly with cleavage activity. Moreover, LAM1desLAM2 is structurally stable and maintains catalytic activity for >3 weeks when stored in SA buffer at 4° C. Importantly, LAM1desLAM2 exhibits minimal activity toward the palindromic LAM1 and LAM2 sites (SEQ ID NOS: 40 and 41 and 44 and 45), indicating that the functional species produced by the method disclosed here is primarily a single-chain heterodimer.

Example 4

Single-Chain I-MsoI Meganucleases Produced Using a Structured Linker

1. Design of Single-Chain I-MsoI Meganucleases Using a Designed, Structured Linker A pair of I-MsoI endonuclease subunits (unmodified with respect to DNA cleavage specificity) were fused into a single polypeptide using Linker 30 from Table 8. Ile-166 was used as the N-terminal fusion point while Leu-7 was the C-terminal fusion point. The resulting single-chain meganuclease, "MSOdesMSO" (SEQ ID NO: 52) was cloned into pET21a with a C-terminal 6×His-tag (SEQ ID NO: 110) to facilitate purification. The meganuclease was then expressed in *E. coli* and purified as described in Example 1.

2. Results

Purified MSOdesMSO was assayed for the ability to cleave a plasmid substrate harboring the wild-type I-MsoI recognition sequence (SEQ ID NO:53 and SEQ ID NO:54 and 54) under the incubation conditions as described in Example 1. The enzyme was found to have cleavage activity comparable to the I-MsoI homodimer (which, in this case, is expected to recognize and cut the same recognition sequence as MSOdesMSO). SDS-PAGE analyses revealed that MSOdesMSO has an apparent molecular weight of ~40 kilodaltons, consistent with it being a pair of covalently joined I-MsoI subunits, and no protein degradation products were apparent. These results indicate that the invention is suitable for the production of stable, high-activity single-chain meganucleases derived from I-MsoI.

TABLE 11

I-CreI Modifications from WO 2007/047859

| | | | | Favored Sense-Strand Base | | | | | | | |
|---|---|---|---|---|---|---|---|---|---|---|---|
| Posn. | A | C | G | T | A/T | A/C | A/G | C/T | G/T | A/G/T | A/C/G/T |
| −1 | Y75 | R70* | K70 | Q70* | | | | T46* | | | G70 |
| | L75* | H75* | E70* | C70 | | | | | | | A70 |
| | C75* | R75* | E75* | L70 | | | | | | | S70 |
| | Y139* | H46* | E46* | Y75* | | | | | | | G46* |
| | C46* | K46* | D46* | Q75* | | | | | | | |
| | A46* | R46* | | H75* | | | | | | | |
| | | | | H139 | | | | | | | |
| | | | | Q46* | | | | | | | |
| | | | | H46* | | | | | | | |
| −2 | Q70 | E70 | H70 | Q44* | C44* | | | | | | |
| | T44* | D70 | D44* | | | | | | | | |
| | A44* | K44* | E44* | | | | | | | | |
| | V44* | R44* | | | | | | | | | |
| | I44* | | | | | | | | | | |
| | L44* | | | | | | | | | | |
| | N44* | | | | | | | | | | |

TABLE 11-continued

I-CreI Modifications from WO 2007/047859

| | | | | | | | |
|---|---|---|---|---|---|---|---|
| -3 | Q68 C24* I24* | E68 F68 K24* R24* | R68 | M68 C68 L68 F68 | | H68 | Y68 | K68 |
| -4 | A26* Q77 | E77 K26* | R77 E26* | | | | S77 Q26* | S26* |
| -5 | | E42 | R42 | | | K28* Q42 | C28* | M66 K66 |
| -6 | Q40 C28* | E40 R28* | R40 | C40 I40 V40 C79 I79 V79 Q28* | A40 A79 A28* H28* | | | S40 S28* |
| -7 | N30* Q38 | E38 K30* R30* | K38 R38 E30* | I38 L38 | | C38 | | H38 N38 Q30* |

Favored Sense-Strand Base

| Posn. | A | Posn. | A | Posn. | A | Posn. | A | Posn. | A |
|---|---|---|---|---|---|---|---|---|---|
| -8 | F33 Y33 | E33 D33 | F33 H33 | L33 V33 I33 F33 C33 | R32* | R33 | | | | |
| -9 | | E32 | R32 K32 | L32 V32 A32 C32 | | | D32 I32 | | S32 N32 H32 Q32 T32 |

Bold entries are wild-type contact residues and do not constitute "modifications" as used herein. An asterisk indicates that the residue contacts the base on the antisense strand.

TABLE 12

I-MsoI Modifications from WO 2007/047859

Favored Sense-Strand Base

| Position | A | C | G | T |
|---|---|---|---|---|
| -1 | K75* Q77 A49* C49* K79* | D77 E77 K49* R75* K75* R79* K79* | K77 R77 E49* E79* | C77 L77 Q79* |
| -2 | Q75 K81 C47* I47* L47* | E75 D75 R47* K47* K81* R81* | K75 E47* E81* | A75 C75 V75 I75 T75 Q47* Q81* |
| -3 | Q72 C26* L26* V26* A26* I26* | E72 Y72 H26* K26* R26* | R72 K72 Y26* F26* | K72 Y72 H26* |
| -4 | K28 Q83 | K28* R28* E83 | R83 K83 | K28 K83 Q28* |
| -5 | K28 C28* L28* I28* | K28* R28* | R45 E28* | Q28* |
| -6 | I30* V30* S30* L30* Q43 | E43 E85 K30* R30* | R43 K43 K85 R85 E30* D30* | K43 I85 V85 L85 Q30* |

TABLE 12-continued

I-MsoI Modifications from WO 2007/047859

Favored Sense-Strand Base

| Position | A | C | G | T |
|---|---|---|---|---|
| -7 | Q41 | E32 E41 | R32 R41 K41 | K32 M41 L41 I41 |
| -8 | Y35 K35 | E32 | R32 K32 K35 R35 | K32 K35 |
| -9 | N34 H34 | D34 E34 S34 | K34 R34 H34 | S34 C34 V34 T34 A34 |

Bold entries are represent wild-type contact residues and do not constitute "modifications" as used herein.
An asterisk indicates that the residue contacts the base on the antisense strand.

TABLE 13

I-Ceu Modifications from WO 2007/047859

Favored Sense-Strand Base

| Position | A | C | G | T |
|---|---|---|---|---|
| -1 | C92* A92* V92* | K116* R116* D116* K92* | E116* E92* | Q116* Q92* |

TABLE 13-continued

I-CeuI Modifications from WO 2007/047859

| Position | Favored Sense-Strand Base | | | |
|---|---|---|---|---|
| | A | C | G | T |
| −2 | Q117 | E117 | K117 | C117 |
| | C90* | D117 | R124 | V117 |
| | L90* | R174* | K124 | T117 |
| | V90* | K124* | E124* | Q90* |
| | | K90* | E90* | |
| | | R90* | D90* | |
| | | K68* | | |
| −3 | C70* | K70* | E70* | Q70* |
| | V70* | | E88* | |
| | T70* | | | |
| | L70* | | | |
| | K70* | | | |
| −4 | Q126 | E126 | R126 | K126 |
| | N126 | D126 | K126 | L126 |
| | K88* | R88* | E88* | Q88* |
| | L88* | K88* | D88* | |
| | C88* | K72* | | |
| | C72* | | | |
| | L72* | | | |
| | V72* | | | |
| −5 | C74* | K74* | E74* | C128 |
| | L74* | K128 | | L128 |
| | V74* | | R128 | V128 |
| | T74* | | E128 | T128 |
| −6 | Q86 | D86 | K128 | K86 |
| | E86 | | R128 | C86 |
| | R84* | | R86 | L86 |
| | K84* | | K86 | |
| | | | E84* | |
| −7 | L76* | R76* | E76* | H76* |
| | C76* | K76* | R84 | Q76* |
| | K76* | H76* | | |
| −8 | Y79 | D79 | R79 | C79 |
| | R79 | E79 | K79 | L79 |
| | Q76 | D76 | K76 | V79 |
| | | E76 | R76 | L76 |
| −9 | Q78 | D78 | R78 | K78 |
| | N78 | E78 | K78 | V78 |
| | H78 | | H78 | L78 |
| | K78 | | | C78 |
| | | | | T78 |

Bold entries are wild-type contact residues and do not constitute "modifications" as used herein.
An asterisk indicates that the residue contacts the base on the antisense strand.

TABLE 14

I-SceI Modifications from WO 2007/047859

| Position | Favored Sense-Strand Base | | | |
|---|---|---|---|---|
| | A | C | G | T |
| 4 | K50 | R50* | E50* | K57 |
| | | K50* | R57 | M57 |
| | | E57 | K57 | Q50* |
| 5 | K48 | R48* | E48* | Q48* |
| | Q102 | K48* | K102 | C102 |
| | | E102 | R102 | L102 |
| | | E59 | | V102 |
| 6 | K59 | R59* | K84 | Q59* |
| | | K59* | E59* | Y46 |
| 7 | C46* | R46* | K86 | K68 |
| | L46* | K46* | R86 | C86 |
| | V46* | E86 | E46* | L86 |
| | | | | Q46* |
| 8 | K61* | E88 | E61* | K88 |
| | S61* | R61* | R88 | Q61* |
| | V61* | H61* | K88 | H61* |
| | A61* | | | |
| | L61* | | | |
| 9 | T98* | R98* | E98* | Q98* |
| | C98* | K98* | D98* | |
| | V98* | | | |
| | L98* | | | |
| 10 | V96* | K96* | D96* | Q96* |
| | C96* | R96* | E96* | |
| | A96* | | | |
| 11 | C90* | K90* | E90* | Q90* |
| | L90* | R90* | | |
| 12 | Q193 | E165 | K165 | C165 |
| | | E193 | R165 | L165 |
| | | D193 | | C193 |
| | | | | V193 |
| | | | | A193 |
| | | | | T193 |
| | | | | S193 |
| 13 | C193* | K193* | E193* | Q193* |
| | L193* | R193* | D193* | C163 |
| | | | D192 | L163 |
| | | | K163 | |
| | | | R192 | |
| 14 | L192* | E161 | K147 | K161 |
| | C192* | R192* | K161 | Q192* |
| | | K192* | R161 | |
| | | | R197 | |
| | | | D192* | |
| | | | E192* | |
| 15 | | E151 | K151 | C151 |
| | | | | L151 |
| | | | | K151 |
| 17 | N152* | K152* | N152* | Q152* |
| | S152* | K150* | S152* | Q150* |
| | C150* | | D152* | |
| | L150* | | D150* | |
| | V150* | | E150* | |
| | T150* | | | |
| 18 | K155* | R155* | E155* | H155* |
| | C155* | K155* | | Y155* |

Bold entries are wild-type contact residues and do not constitute "modifications" as used herein.
An asterisk indicates that the residue contacts the base on the antisense strand.

The invention claimed is:

1. A recombinant single-chain meganuclease comprising:
(a) a first subunit comprising a polypeptide having at least 85% sequence identity to residues 9-151 of SEQ ID NO: 1;
(b) a second subunit comprising a polypeptide having at least 85% sequence identity to residues 9-151 of SEQ ID NO: 1; and
(c) a polypeptide linker, said polypeptide linker being covalently bound to said first and said second subunit;
said first subunit being covalently bound to said polypeptide linker at a residue corresponding to a position selected from the group of positions 153-163 of SEQ ID NO: 1;
said second subunit being covalently bound to said polypeptide linker at a residue corresponding to a position selected from the group of positions 1-9 of SEQ ID NO: 1;
wherein said polypeptide linker is SLPGSVGGLSPSQASSAASSASSSPGSGISEALRAGATKS (SEQ ID NO: 77);
wherein said first and second subunits are capable of functioning together to recognize and cleave a non-palindromic DNA sequence.

* * * * *